(12) United States Patent
Holm-Kennedy

(10) Patent No.: US 7,566,418 B2
(45) Date of Patent: Jul. 28, 2009

(54) BIOCHEMICAL CONCENTRATOR AND DRUG DISCOVERY

(75) Inventor: James W. Holm-Kennedy, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 11/083,107

(22) Filed: Mar. 18, 2005

(65) Prior Publication Data

US 2005/0208647 A1    Sep. 22, 2005

Related U.S. Application Data

(60) Provisional application No. 60/554,614, filed on Mar. 18, 2004.

(51) Int. Cl.
| | |
|---|---|
| C12M 1/00 | (2006.01) |
| G01N 27/26 | (2006.01) |
| B01J 19/12 | (2006.01) |
| C12Q 1/68 | (2006.01) |
| G01N 15/06 | (2006.01) |
| H01M 10/48 | (2006.01) |
| G01N 33/566 | (2006.01) |
| C12Q 1/00 | (2006.01) |
| G01N 33/53 | (2006.01) |
| C12M 1/34 | (2006.01) |

(52) U.S. Cl. ............ 422/68.1; 204/403.01; 204/403.03; 204/193; 204/400; 422/50; 429/92; 436/501; 435/4; 435/7.1; 435/287.1; 435/287.2

(58) Field of Classification Search ............ 204/403.01, 204/403.03, 193, 400; 422/50, 68.1; 429/92; 436/501; 435/4, 7.1, 287.1, 287.2
See application file for complete search history.

(56) References Cited

U.S. PATENT DOCUMENTS

| | | |
|---|---|---|
| 4,885,623 A | 12/1989 | Holm-Kennedy et al. |
| 4,916,505 A | 4/1990 | Holm-Kennedy |
| 4,926,682 A | 5/1990 | Holm-Kennedy et al. |
| 4,926,693 A | 5/1990 | Holm-Kennedy et al. |
| 4,951,510 A | 8/1990 | Holm-Kennedy et al. |
| 4,960,177 A | 10/1990 | Holm-Kennedy et al. |
| 5,036,286 A | 7/1991 | Holm-Kennedy et al. |
| 5,083,466 A | 1/1992 | Holm-Kennedy et al. |
| 5,095,762 A | 3/1992 | Holm-Kennedy et al. |
| 5,101,669 A | 4/1992 | Holm-Kennedy et al. |
| 5,140,393 A | 8/1992 | Hijikihigawa et al. |
| 5,466,348 A | 11/1995 | Holm-Kennedy |

(Continued)

FOREIGN PATENT DOCUMENTS

WO    WO 01/64945    9/2001

*Primary Examiner*—Bao-Thuy L Nguyen
*Assistant Examiner*—Jacqueline Diramio
(74) *Attorney, Agent, or Firm*—James Creighton Wray; Meera P. Narasimhan

(57) ABSTRACT

A novel label-free sensitive detection method by employing a novel sensitive charge sensor is provided. Dissociation constant information is provided by a simple measurement of the dissociation of the target molecule form the target's receptor. The later process is affected by a novel system and its configuration as described herein. Basic objectives are to provide a drug discovery and characterization system that is an improvement over the current state of the art, low cost, highly sensitive, accurate, fast and easy to use. This invention involves both a physical system and a methodology.

4 Claims, 21 Drawing Sheets

U.S. PATENT DOCUMENTS

| | | |
|---|---|---|
| 5,784,507 A | 7/1998 | Holm-Kennedy et al. |
| 6,600,031 B1 * | 7/2003 | Fodor et al. ............... 536/24.3 |
| 2004/0011650 A1 * | 1/2004 | Zenhausern et al. ......... 204/547 |
| 2005/0009066 A1 * | 1/2005 | Connolly ...................... 435/6 |

* cited by examiner

● Negatively charged biochemical or other negative ion.

E Electric Field

- Negatively charged biochemical or other negative ion.

E Electric Field

Concentration of Negatively Charged Target Molecules ( ● )

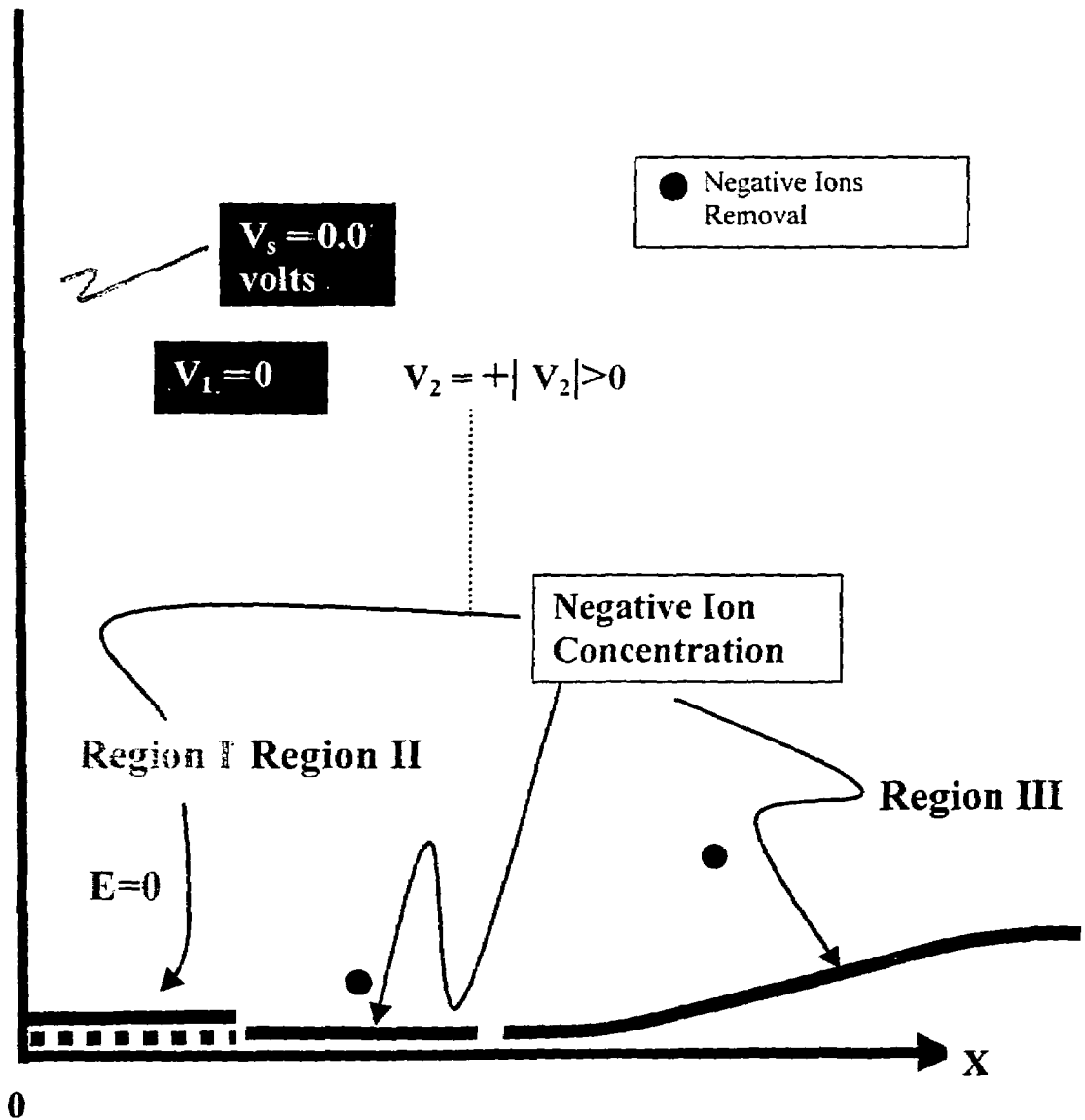

BIOCHEMICAL CONCENTRATOR AND DRUG DISCOVERY

This application claims the benefit of U.S. Provisional Application No. 60/554,614, filed Mar. 18, 2004, which is hereby incorporated by reference in its entirety.

BACKGROUND OF THE INVENTION

There is a need for a simple, reliable, sensitive, easy means of measuring accurately the dissociation details between two molecules; for example, the dissociation constant between a protein and a DNA or RNA molecule. In general, drug efficacy requires that the binding between the drug and the drug's targeted receptor or molecule be strong.

There is a need for a simple, reliable, sensitive easy means of concentrating chemicals, in particular biochemicals. One area of need includes the immediate region of a biosensor where target concentration can directly affect the binding concentration of target to recognition elements, or receptors, on the surface of a sensor element.

There is a need for a means to improve the concentration of target molecules in the vicinity of a sensor element, i.e. the delivery of said target molecules to the reaction (binding) region of a sensor element without the presence of an electric field that may alter binding details.

There is a need to be able to determine the target concentration in a sample solution. The present invention also has significant utility in determining target concentrations in solution.

Thus, testing for drug discovery requires measurement of the dissociation constant(s) and related dynamics. Drugs must bind to their targeted drug receptors and typically remain bound for some reasonable duration for the drug to be efficacious.

There are two major problems in drug discovery that are addressed by the present invention: (1) the very low concentration of proteins and chemicals pertinent to drug efficacy, studies and discovery, and (2) the need for a fast, straightforward, and low labor method of testing drug molecule appropriate binding details.

There are major problems also associated with biosensing target detection, identification and quantification, where target concentrations are low and which are addressed by the present invention:

1. The very low concentrations of target molecules needed to bind to a sensor for subsequent detection.
2. The potential influence of a strong electric field in proximity to a target molecule or receptor element where said electric field may later certain biochemical geometries with the possible alternation of specificity and binding details. There is a need for an improved field free target to sensor delivery means and field free target to receptor binding environment.

The term "receptor" here is intend to be interpreted in it's most general sense. A receptor, as referenced in this document, means a chemical binding site that is specific to the binding of a particular chemical (target chemical). Thus, the term "receptor" as used in this application in intended to be a generic term referring to a "recognition element" where recognition specificity is associated with the type of chemicals targeted. Thus, proteins, oligos, c-DNA, and many other chemicals constitute a "receptor" in the spirit of this document.

A common method of measuring the dissociation constant of two bound molecules, receptor and target, is to measure the concentration of bound molecules as a function of concentration of the target molecule. Fluorescence methods are often used, but require additional processing and may interfere with binding details.

An additional problem with current methodologies is the requirement for attaching a label, such as a fluorescence label, that may influence binding. Use of labels also adds processing time and cost to the testing and discovery procedure. Labels are undesirable and should be eliminated where possible. Another issue with fluorescence labeling during identification bound molecules is biochemistry complexity. Furthermore, the costs associated with fluorescence instrumentation are very high. Any additional chemical processing adds cost and labor, and is thus quite undesirable if it can be avoided. The invention may be used with such labeling if needed.

Needs exist for faster, more efficient and reliable biochemical concentrators and drug discover. A simpler, less labor intensive and label free method is needed. There is also a need for improved chemical target detection speed and signal strength.

SUMMARY OF THE INVENTION

For purposes of this disclosure, receptor is meant to have a broader definition that includes all forms of recognition elements.

For rapid drug discovery, besides the ease of measuring binding details, it is important to test many compounds with many receptors simultaneously, i.e. many tests proceed simultaneously. This is accomplished by using a sensor array. If many compounds are tested simultaneously, then a second test where the drug candidates are rebound is used to mine the target potential drug molecules. Once bound to the receptors on a particular sensor in the sensor array, the system is washed clean and then the dissociation affected. The residual molecules in solution are the molecules bound to one or more particular receptors. Thus, one can test many drug candidates with many receptors simultaneously, and recover the potentially efficacious drug if a suitable sensor and suitable concentration-environment-monitoring devices are found. Additionally, the testing for efficacious drugs is best performed without chemical processing to attach labels, such as fluorescent labels.

The invention addresses a solution to this collection of problems. Employing a novel sensitive charge sensor provides a novel label-free sensitive detection method. Dissociation constant information is provided by a simple measurement of the dissociation of the target molecule form the target's receptor. The later process is affected by a novel system and its configuration as described herein. The invention also addresses a solution to the problem of speed and concentration related measurement issues associated with detection of target molecules. The invention also address target concentration measurement issues.

Basic objectives are to provide a drug discovery and characterization system and a target detection system that is an improvement over the current state of the art, low cost, highly sensitive, accurate, fast and easy to use. This invention involves both a physical system and a methodology.

An important aspect for development of efficacious drugs to treat a multitude of diseases is the strength of binding of a potential drug to an appropriate drug binding site. Further, such chemical binding is an important aspect of protein function in human health and condition. However, such proteins may be low in concentration.

An objective of the invention is to provide a system and method to determine binding energy or energies, kinetics and details by use of an appropriate low cost sensor and sensing mechanism together with a system that provides a testing environmental condition that controls the target molecule concentration in pre-selected ways to affect the measurements in a controlled and meaningful manner, as described below.

A further objective of the invention is to provide a system and method for concentrating target molecules in the immediate vicinity of a sensor's recognition elements for improvement of detection reliability, detection speed and improvements in specificity reliability.

These and further and other objects and features of the invention are apparent in the disclosure, which includes the above and ongoing written specification, with the claims and the drawings.

BRIEF DESCRIPTION OF THE DRAWINGS

FIG. 2D shows target molecules free carrier concentration steady state for conditions shown in FIG. 1C.

DETAILED DESCRIPTION OF THE PREFERRED EMBODIMENTS

Figure 1A:
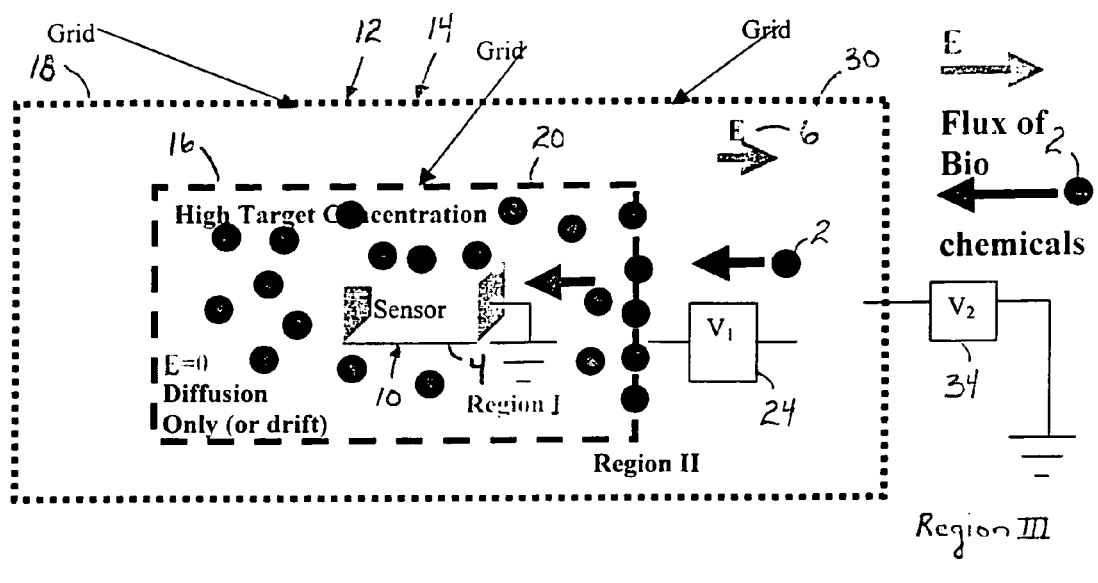
FIG. 1A is a Region I Concentrator, which is an ion or species concentrator or de-concentrator.

In using a sensor to detect a biochemical specific target, the target concentration can play a major role in the sensor's detection success, and in speed of response. The rate of binding of a target to a biochemical or chemical receptor is directly related to the concentration of the target. The higher the target concentration, generally, the higher the target attachment binding concentration and target-receptor attachment rate, and thus, the faster the sensor response. Two basic critical binding rate situations are common. They relate to the concentration of target molecules in the immediate vicinity of the receptor to which they will bind.

The first is reaction limited binding where the target concentration is sufficiently high so there is adequate concentration (density) of the target to support continuing chemical attachment reactions. Here, the rate of attachment is receptor concentration limited.

In diffusion limited binding low binding rates and related problems exist. When the concentration of target molecules is low, the supply in the immediate vicinity of the binding receptor can be consumed rapidly, depleting the target resource. In this case, more target molecules must be supplied via whatever transport mechanism is acting. That transport mechanism is usually either diffusion or eddy currents and turbulence. Since the binding rate is controlled by how fast the target molecules arrive at the receptor binding location, the features of the supply mechanism become important. If the initial binding of the target molecules present in proximity to the receptors provides too low of a bound concentration (target-receptor molecule) for the sensor to measure the binding, additional binding and thus additional target molecules are required for the sensor sensitivity to detect and measure the target presence. More target molecules must be delivered to the remaining receptors or measurement portion of the sensor. Turbulence can be used to improve the situation but has problems in that the target molecules may be swept past the receptors too quickly for binding. Diffusion is a process that is always present when there is a target concentration gradient, as there is if some of the target molecules are depleted by receptor binding reactions. Thus, a principle transport of such additional target molecules to the unbound receptor, absent some delivery force, is by diffusion. To exploit the diffusion features, it is important to understand the basic features that controls how quickly target molecules diffuse to a receptor region. The diffusion transport mechanism can be manipulated, as is shown in certain invention embodiments described herein. To understand how those embodiments function and provide improve target binding rates, some discussion of the fundamentals of the diffusion process is helpful.

Diffusion occurs by a random walk process delivering the diffusing species (target in this case) from a high target concentration to a lower concentration region. The transport is characterized macroscopically by diffusion constant "D". Diffusion is a well-known process and the transport is in typically presented analytically by:

$$\text{Flux} = -D \times \nabla \text{Concentration} \quad \quad \text{Equation 1}$$

Here $\nabla$ is a derivative in three dimensions, and "x" is the multiplications sign.

The rate of diffusion transport is called diffusion flux, in units of number per unit area per second. This flux is directly proportional to the slope of the concentration, i.e. to the concentration gradient; with proportionality constant D termed the diffusivity. The diffusivity represents the microscopic details of the transport in a macroscopic constant that is dependent on environment and species features such as mass and shape.

Equation 1 has serious implications with respect to sensor speed when target concentrations are small, as they often are with some molecules in some environments. Toxins, such as botulinum toxin, are an example where low concentrations kill, but are so low that they are hard to detect. The origin of a portion of the low target concentration detection problem that leads to low binding rates is that for low target concentrations the target concentration gradient is very small. Small concentration gradients result in low transport rates of target molecules to the binding receptors. Thus, the rate of binding of target to receptor is very slow for low target concentrations, not just because the concentrations are low, but because the delivery of additional targets to the binding site is very slow. The lower the target concentration, the slower the diffusion delivery of target molecules to the receptors. The result is a slow binding rate of target to receptor and a related slow response rate of the sensor.

Sensor speed is of central importance for the timely detection of some target molecules such as botulinum, anthrax and other toxins. A slow sensor response can translate into a tardy warning. The problem needs a solution. Some manner of concentration of target molecules in the immediate region of the specific target's receptors is needed to increase the binding rate.

A low concentration of target molecules is also problematic when low bonding concentration cause low sensitivity of sensor detection. At low target concentrations in the sensor's environment, not all of the receptors will bind to target molecules, target molecules presence notwithstanding. The issue is very serious for targets that are very toxic, or require only low densities to be hazardous, for example, in bioterrorist threat agents. In other cases, by way of example, where a target protein or other chemical is of low concentration or where the test sample is small, the issue also arises. Such situations arise in forensics and human and plant pathology.

The origin of the problem is related to a fundamental physical process called "mass action". Mass action effects on molecular binding to the receptors concentrations are discussed herein. The mass action law, as exhibited in chemistry, addresses the fact that two reacting chemical species, S1 and S2, experience simultaneous competing rates of binding and dissociation. These competing actions ultimately influence the equilibrium or steady state bound or product concentration. For a simple case of two chemical reacting species (reactants), S1 and S2, of concentration $N_1$ and $N_2$, respectively, S1 and S2 react to form a product P. The relationship between $N_1$, $N_2$ and their product concentration $N_P$=[S1S2] is represented simply by the "mass action" equation:

$$[P]/N_1 \times N_2 = K(T) \qquad \text{Equation 2}$$

Here K(T) is a temperature dependent constant characterizing the relationship between the concentrations $N_1$ and $N_2$ of two species S1 and S2, respectively, and [P] concentration of their product P=S1S2. $N_1$, $N_2$ and [P] represent the related chemicals' concentration per unit volume or molar concentrations.

Equation 2 means that the binding relationship between constituent species S1 and S2, resulting in a bound compound S1S2, is dependent upon concentrations.

Rewriting Equation 1, $$[P] = \frac{N_1 \times N_2}{K(T)} \qquad \text{Equation 3}$$

The bound product is dependent upon the each species' (S1 and S2) individual concentrations, and on the dissociation constant K(T). The smaller K(T), the larger the concentration of bound product [P]. Different chemical species and products have different dissociation constants. For example, different antibodies to a particular target may exhibit different dissociation constants. Examples of species of interest in biochemistry include, but are not limited to, antigen-antibody products, DNA, RNA and protein products. Binding to chemicals such as Pb, Hg and botulinum toxin exhibit similar dissociation relationships. The mass action law is a general concept describing a common chemical phenomena.

Mass action has an effect on sensor target detection sensitivity. An important issue for some biochemical sensing, because of the mass action phenomena, is the effect on bound product concentration [P] when one or both of the reactant concentrations [S1]=$N_1$, and [S2]=$N_2$ are very low. This situation can occur, by way of example, for low concentration targets where the low concentration is sufficient to have an influence on the system of interest, such as the human body. For example, botulinum toxin is deadly at very low concentrations in water. Lethal concentrations are very low molar concentrations, i.e. they require only a modest number of botulinum molecules. Viruses constitute a further example, and nerve gases another. If the concentration N1 of a target species S1 is low, then it can be shown, using Equation 3, that the percentage of target receptors to which there is binding [P] is very low and can be a very small fraction of the actual receptors present. In the case of botulinum toxin binding to an antibody, with a reported dissociation constant, the binding may be to less than 1 antibody in one thousand (<1/1000) even though there are remaining molecules in the immediate vicinity of the unbound antibodies. Thus, a sensor would have its "anticipated" sensitivity reduced by a factor of 1000 in this case if the mass action phenomena were ignored. The sensor's detection ability is improved by increasing the number of receptors (same binding percentage, just more signal) or by choosing receptor/target pairs that have strong binding (low values of K). However, one expects a limit to the density of receptors that may be attached to sensors. This basic limitation puts high demands on the sensitivity of the sensors being used. For example, if fluorescence methods are used to detect the bound pair, the light signal may be very weak and push the limits of optical detection technology, or may simply be below that level of signal that can be reasonably measured.

If there is a sensor sensitivity issue involved, as is the case, by way of example, for sensing/detecting a lethal threshold concentration of botulinum toxin, one must find a way to increase the concentration of the target molecule to increase the concentration of the product molecules and affect the product detection. Where the general target concentration is very low a biochemical concentrator system and/or methodology is needed. Ideally, such a concentrator would provide maximum utility if it could be easily integrated with the detection systems and require no additional or extensive processing of the host material or additional of chemical reagents. That is, if one can increase target concentration $N_1$, the bound pairs P are increased and thus the sensor output signal is also increased.

Such target concentration is problematic from several points of view. Primarily, one does not want to create any significant delays in sensing the target agents. Thus, one needs a device that is fast. Cost is an issue. Ease of use is important. Manufacturability is also important.

Collection enhancement is used in the present invention. Since the collection is dependent on the force on the molecule derived through the influence of the applied electric field (Force=Q×E), improved concentration is affected by increasing the charge on the target species S1. This results in lower voltage requirements, faster target accumulation, and higher target concentrations in the vicinity of the sensing means. For example, DNA fragments may be added to an antibody target chemical to increase the net charge associated with the target chemical species S1.

While the invention is discussed herein in terms of a solid-state transducer, the invention has utility wherever there is a need to concentrate a chemical target species. Examples include, but are not limited to, proteins, toxins, viruses, bacteria, fungi, DNA components, RNA components and particles. Where the target species is not charged, a bound charge can be attached using chemical means known to those of skill in the arts.

For sensing molecules at low concentrations, one needs to have the highest target concentration possible. This affects two basic issues arising from the details of the binding of target to receptor, which are key to solving the problem:

1. Rate of binding of target S1 to the receptors (or, in general second reactant species S2).
2. Rate of delivery (transport) of the target molecules S1 to the binding molecules S2, and thus to the immediate environment vicinity of the binding molecules S2.
3. Concentration of the target molecules $N_1$ in the receptor region. This influences the equilibrium maximum bound target/receptor concentration [P] (=P) through mass action phenomena. A high concentration $N_1$ creates a high product concentration thereby providing a strong sensor output signal.
4. Rapid binding of the target molecules to the receptors to ensure a strong sensor signal indicative of the presence of the target molecule in as short a time as feasible.
5. Non-specific reaction enhancement or adverse influences are to be avoided.

This invention provides an electric field assisted, biochemical target concentrator system. Most biochemicals carry a charge or can be made to carry a net charge. If a target molecule does not carry charge, charge can be added through chemical means. Charged molecules can be moved or transported by an electric field. Diffusion processes can also transport charged and uncharged molecules. An electric field is generated using a battery or power supply source. The electric field can be: DC, AC, sinusoidal, pulsed, or other types.

Objectives of the invention are to drift or diffuse or drift and diffuse the target molecules to the immediate vicinity of the sensor receptors, and to increase the target molecule in the vicinity of the sensor receptors for increasing binding rates and increasing binding populations, while not adversely affecting the specificity of the binding molecules, neither receptors nor the targets.

Drift of a target species can be expressed in terms of charge transport using the equation:

$$V_d = \bullet E \quad \text{Equation 4A}$$

Here, $$\bullet = q \blacktriangledown / M \quad \text{Equation 4B}$$

Where q is the charge on the molecule, ▼ is a measure of the viscous drag of on the motion of the molecule, and M is the mass of the molecule.

Here $V_d$ is the drift velocity, and ● is the mobility and E is the electric field. The flux of target molecules responding to the drift electrical force is $$F_1 = N_1 V_d \quad \text{Equation 5}$$

The higher the electric field E, the higher the flux of target molecules delivered to the terminal location of the Electric field.

Using AC and pulsed electric field implementation, the voltages creating the electric fields of interest may be of either polarity. The voltages may also have a time dependent character. Both of these features have utility in the invention described herein.

Different chemical species, such as biochemicals, may have different charges and typically have different mass and geometrical features. The former affects the force influencing the molecules transport. The latter two features, mass and molecule geometry, influence the drift mobility ●, see Equation 4B. Selective use of pulsed voltages may be used to help separate different chemical species. Here the drift of the different species affects their location and delivery rate. This feature may be used to affect some pre-selection of species. For example, a group of different species may be present and acquired via the collection means described herein. By way of example, light mass species of no interest in this example may be repelled faster than the heavy molecules. This invention has means of providing separation of these species. Other techniques for controlling concentration details are provided. AC and pulsed voltages and electric fields have different effects on species with different charges and mobilities. Such features are exploited in selective concentration schemes.

By using "opposite polarity" electric fields, voltage polarities may be used to control the concentration of selected species. For example, positive and negatively charged molecules drift in different directions. Positive voltage polarities have the opposite force effects on transport of a chemical species having a particular charge.

One objective of the present invention is to track the dissociation of the bound target molecules attached to a sensor surface, as shown in FIG. 1, as a function of time and relate this to the binding dynamics. The decay of the sensor signal as the target dissociates, and is removed from the vicinity of the sensor, as indicated in FIG. 2E, provides a direct measure of the molecular pair, or of multiple components if more than two molecules are involved, dissociation features including the dissociation constant(s) of the target-receptor pair. Thus, the tracking of the dissociation provided compound binding information to a protein, receptor, DNA, RNA or some other compound. The removal of the target from the sensor vicinity when the target dissociates creates decay that is a direct measure of the binding features of the target. Such information on binding strength and dissociation details is a key to drug discovery. While a decay of signal may be used for various transducer signals, such as fluorescence, florescence requires additional processing that may distort the binding details. Fluorescence in general is not a good method for dissociation constants as the potential interference with the dissociation mechanics may be problematic and provide erroneous results, the prevalence of fluorescence measurement notwithstanding. The invention is suitable for use with a multitude of sensor systems employing various sensing mechanisms.

A much better type of sensor to use for this application is a charge sensor or a chemical potential sensor because many biochemical molecules are charged.

One issue with binding dissociation measurements is the need to incorporate a means for both ensuring saturation or near saturation of the receptor molecules and then the removal of dissociating target molecules.

The innovation of the present invention addresses a means for creating a saturated or well-bound population of target molecules, and a means for removing the dissociating target molecules from the vicinity of the sensor.

One objective of the invention is to provide a device which can first create a high concentration of pre-selected biochemicals in the immediate vicinity of a biosensor, if needed, see FIG. 1A. The device then supports attachment of the pre-selected target biochemical to a receptor or complimentary selective binding molecule that has been previously bound to the sensor surface. The second function is to remove the target biochemicals from the region surrounding the biosensor, Region I, FIG. 1B, after full binding has occurred. The latter sets up a condition where the dynamics of the dissociation of the target molecule from the receptor are characterized and measured.

Figure 1B:
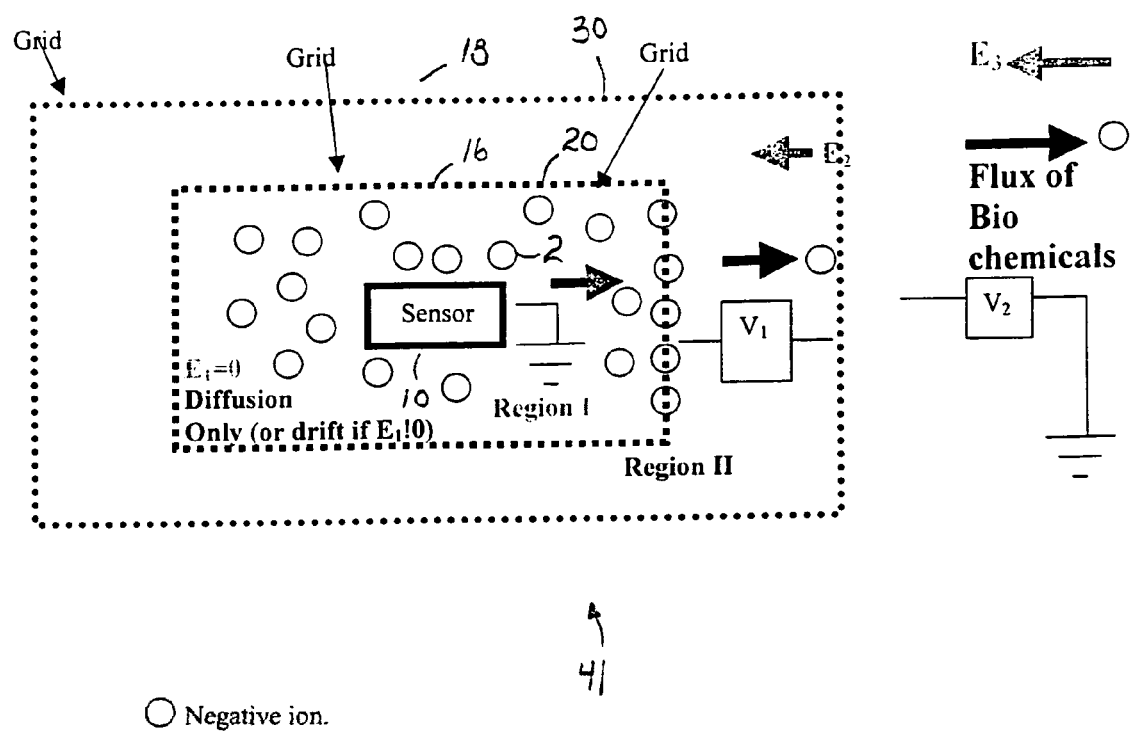
FIG. 1B shows a Region I biochemical removal device.
Figure 1C:
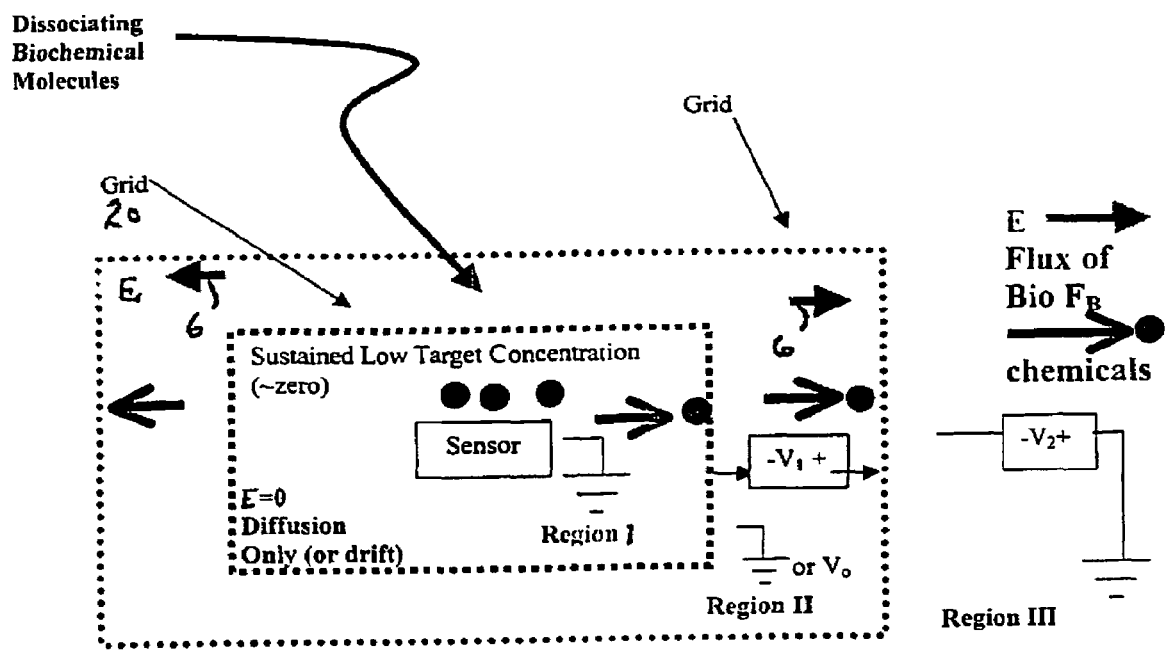
FIG. 1C shows Region I ion removal as target biochemicals dissociate from the sensor surface.

Here, as shown in FIG. 1B, the target molecules are removed quickly from the vicinity of the sensor, thus, eliminating any rebinding of the target to the receptor, see FIG. 1C.

Given a subsequent absence of the target molecule, see FIG. 1C, the target dissociation from the receptor is controlled only by the dissociation rate process and the dissociation proceeds. Those target molecules remaining bound to the sensor receptors are monitored over time by simply monitoring the sensor signal. Thus, a chemical dissociation curve is measured, as shown in FIG. 2E. This curve provides the dissociation rate and constant(s) of the receptor-target pair.

Such dissociation and binding strength information is pertinent to the identification and discovery of efficacious drugs. Binding of protein-to-protein, protein to receptors, protein to nucleic acid molecules (RNA and DNA, for example) and binding of molecules to drug target sites are examples.

Two conditions are intended be affected by the invention apparatus.

Figure 3:
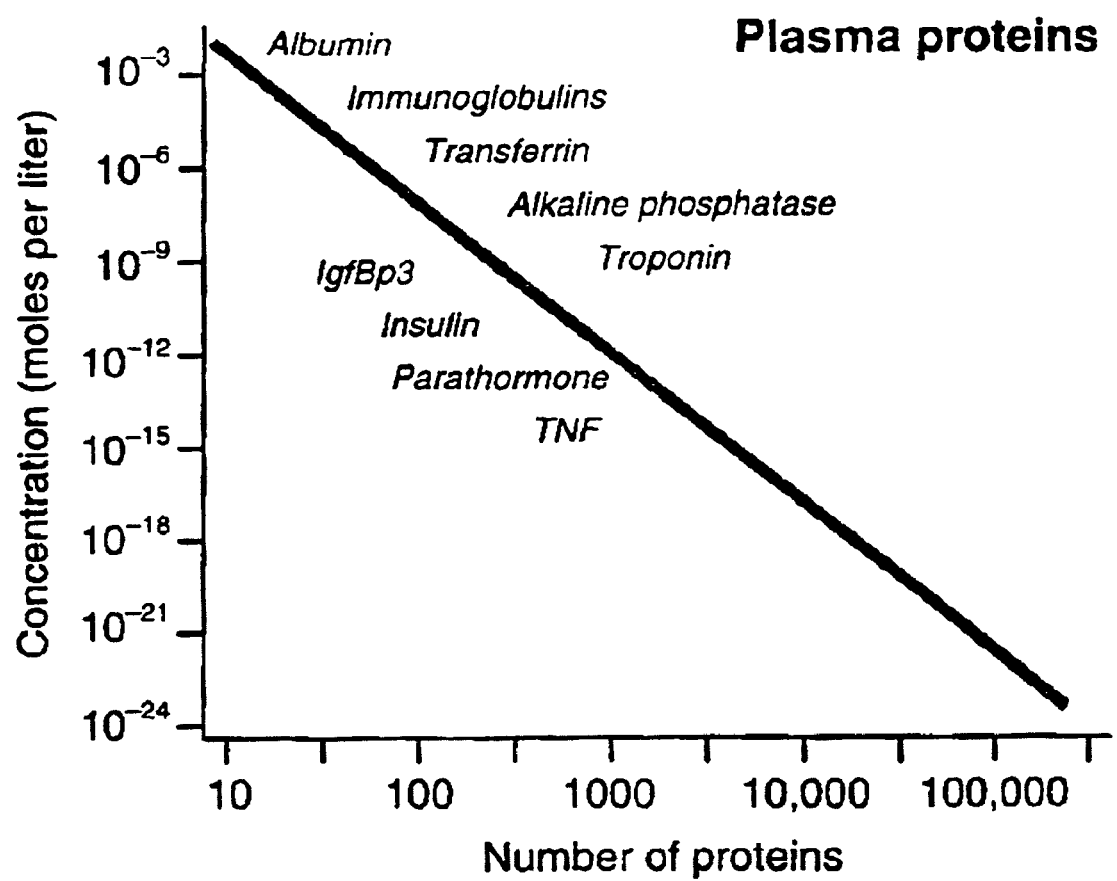
FIG. 3 shows protein concentration, in molar concentration, in blood plasma versus the number of proteins.

Increasing the concentration of the target biomolecules in Region I, as shown in FIG. 1A, ensures that binding occurs. Increasing the concentration of biochemicals in the vicinity of the sensor is a significant problem. The solution of the present invention, as shown in FIG. 1A, is non-obvious. It is noted that some biochemicals are of very low concentration as found in nature, e.g., in blood plasma. FIG. 3 shows a reported concentration of proteins versus number of proteins in human blood plasma. A large number of proteins are found in only very small concentrations in plasma. That situation is a significant problem in proteomics in general and in drug discovery in particular. Techniques such as mass spectroscopy require a large number of molecules in order to detect them, and the instrument cost is very high.

Where one wishes to study the binding features of receptors to low-density targets such as in a large number of proteins, as shown in FIG. 3, one must also use a receptor-target binding system which can be measured. There is a fundamental problem associated with such receptor binding. The dissociation constants vary and in general are not strong enough to assure significant steady state binding where the target concentrations are low. That phenomena is described by the mass action law which relates the rate of receptor-target binding to receptor-target dissociation. The essence of this law is: where the concentration of the target molecule molar concentration, such as a protein, falls too low, there is reduced binding, and thus reduced detection by the sensor or by some receptor in the human body, for example. The binding may be nearly zero if the target concentration is sufficiently low. By way of example, if a receptor-target dissociation constant is $10^{-9}$, about half of the complimentary binding pairs ("receptors") are bound at $10^{-9}$ molar concentration of target molecules. This translates to a low detection signal for many sensors, and may fall well below the detection capabilities of some sensing means. That situation is problematic in testing for drug efficacy in many instances since, although desired drug candidates may be binding or affecting binding, the concentration may be far too low to measure. Thus, the potential drug efficacy is missed.

The present invention provides a solution to the problem of inadequate target molecule binding density by increasing the concentration of the target molecule in the vicinity of the binding complementary molecule receptor. What is provided, in addition to a sensitive sensing device, is a device for concentration the target chemical in the vicinity of the sensing device containing the receptors to the target molecule.

With saturation, near saturation, or significant binding of the target molecule to the receptor, arising from adequate concentrations of the target molecule in the immediate vicinity of the receptor, a significant detection signal indicating the binding is measured with a suitable sensor. Subsequent removal of the target molecules from the vicinity of the sensor creates a condition causing a new decrease in bound target molecules arising from simple dissociation. The sensor quantitatively measures the remaining bound target density, and thus the dissociation rate and related parameters are determined from this simple measurement. That is, if the concentration of target molecules is reduced to near zero and well below the concentration indicated by the dissociation constant, the bound target molecules dissociate from their complementary binding molecule, attempting to restore the equilibrium concentration dictated by the mass action law. If the dissociated target molecules are removed from the sensor, Region I in FIG. 1, then as soon as they are released the dissociation exhibits an exponential decay characteristic of the details of the binding strength between the target molecule and its complementary receptor. If multiple binding features are present, then the decay curve, as shown in FIG. 2E, shows some "structure" that is analyzed for the various dissociation constants and binding involved. Using this approach, the strength of the binding is measured.

The central application of the device of FIG. 1A-D, i.e. after concentration and binding has occurred, is to remove target biochemicals from a pre-selected Region I, as shown in FIG. 1. This function has many useful applications. By way of example, the device may be used in: dissociation constant measurement to measure dissociation dynamics and binding energies of chemical pairs, drug discovery, where the strength of the binding of a potential drug molecule to its target site is an important consideration in the efficacy of the drug to treat some disease or affect some biochemical process, and protein binding and dissociation features, where protein binding to other proteins and to RNA and DNA is important. Binding strength is an important related parameter in biochemistry processes in the body. Such binding is pertinent to disease diagnostics and drug discovery.

The process is described above and illustrated in FIGS. 1 and 2.

The concentrator/de-concentrator device is a physical structure. The function of the structure is to move pre-selected chemicals, e.g., biochemicals, into or out of a particular region, such as Region I in FIGS. 1A, 1B and 1C. By way of example, Region 1 in FIG. 1 may contain a sensor 10, another instrument, one or more specific receptor chemicals for specific targets, chemical binding, or other component. In this case of the invention used as a chemical removal device, pre-selected target molecules can be removed from Regions I, II and III at pre-selected removal rates. Alternatively, the target biochemical concentration of Region I may be maintained at a pre-selected concentration whether said concentrations are zero or some finite value. This function has significant utility in the study of biochemical binding, medical technology, drug discovery and biodefense. The invention also has significant utility in determining target concentrations in solution.

Here the biochemicals are assumed charged. The charge may be naturally occurring or arising from a chemical attachment where said additional chemical attaching to the biochemical carries a net charge with it. Indeed, the sensitivity of the detection may be improved by attaching such chemical tags carrying substantial charge. An example is attaching a length of DNA that is reported to have about two charges per base pair. Such "charge amplification" means is described in a separate invention in more detail.

A preferred embodiment places a sensor in Region I in FIGS. 1A, 1B and 1C and controls the concentration of pre-selected biochemicals in Region I through a cage structure 12 comprising a set of grids 14, located at the interfaces between Regions I and II, grid 20, and Region II and III, grid 30. Here the grids are electrodes to which voltages are applied from a power supply or battery. The grids are biased with predetermined voltages $V_1$ and $V_2$ from sources 24, 34 suitable for the desired biochemical transport by drift, and diffusion where the electric field E is zero in FIG. 1, or not, depending on the target transport function desired. Voltages may be applied to the various grids resulting in pre-selected electric field 6 in the different regions, polarities and magnitudes selected to provide the biochemical transport desired. Positively charge molecules move in one direction, and negatively charge molecules move in different directions under the influence of electric field E. The directions are determined by the electric field orientation. In the case of zero field regions, the molecules can move by diffusion with the diffusion flux F given by:

$$F_B = -\textcircled{x} N_B(x, y, z, t) \quad \text{Eq. 1}$$

$F_B$ is the flux of biochemical molecules, and $N_B$ is the biochemical molecule concentration as a function of location x, y and z a time t.

Where an electric field is present, transport is by drift:

$$F_{drift} = N_B \bullet E$$

Here ● is the molecules mobility and E is the electric field arising from the voltages applied to the grids.

The voltage and electric field details are selected so as to accumulate or remove target molecules from the proximity of the biosensor. In this embodiment of FIGS. 1B and 1C of the present invention, the voltages applied to generate fields that transport negatively charge ions out of Region I and other pre-selected Regions. By way of example, in the FIGS. 1B and 1C, for sake of discussion, it is assumed that the charged biochemicals of interest have a net negative charge and thus move in the direction opposite to the applied electric field. For removal of positive ions, the voltage and electric field polarities are reversed.

FIG. 1C shows the condition where Region I has been made essentially void of the target molecules. As soon as another molecule dissociates from its receptor, it is removed from Region I by drift or diffusion transport means. Thus, the rate of dissociation is measured directly by the sensor.

Figure 1D:
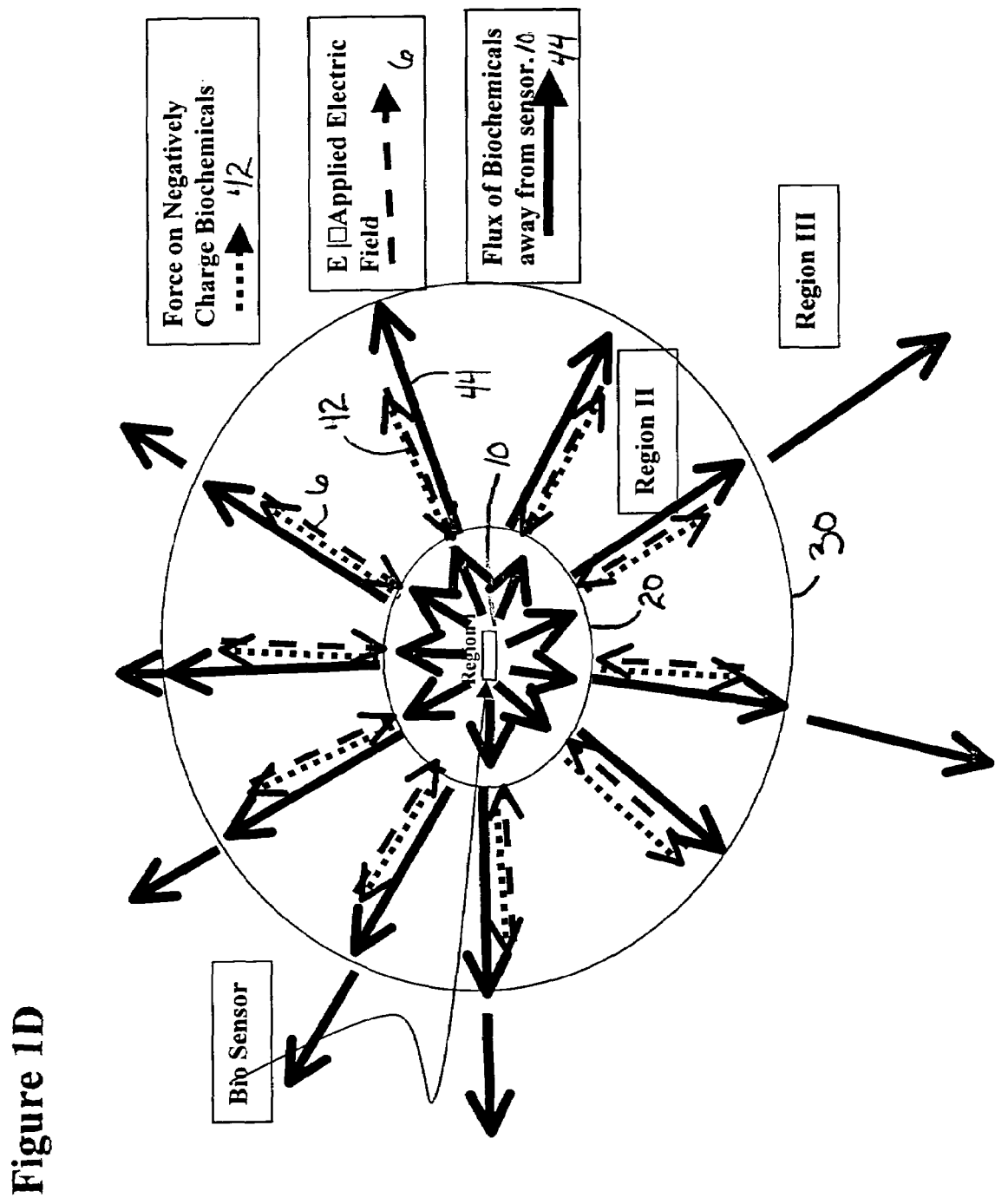
FIG. 1D shows a two grid spherical biochemical removing device.

FIG. 1D shows another geometry for the chemical concentrator/removal system. This system works similarly to that shown in FIGS. 1A, 1B and 1C. One difference in the system of FIG. 1D is that the electric field is no longer essentially homogenous in most regions as it was for rectangularly arranged grids. This can be advantageous in the removal or concentration of the charged chemicals.

Figure 2A:
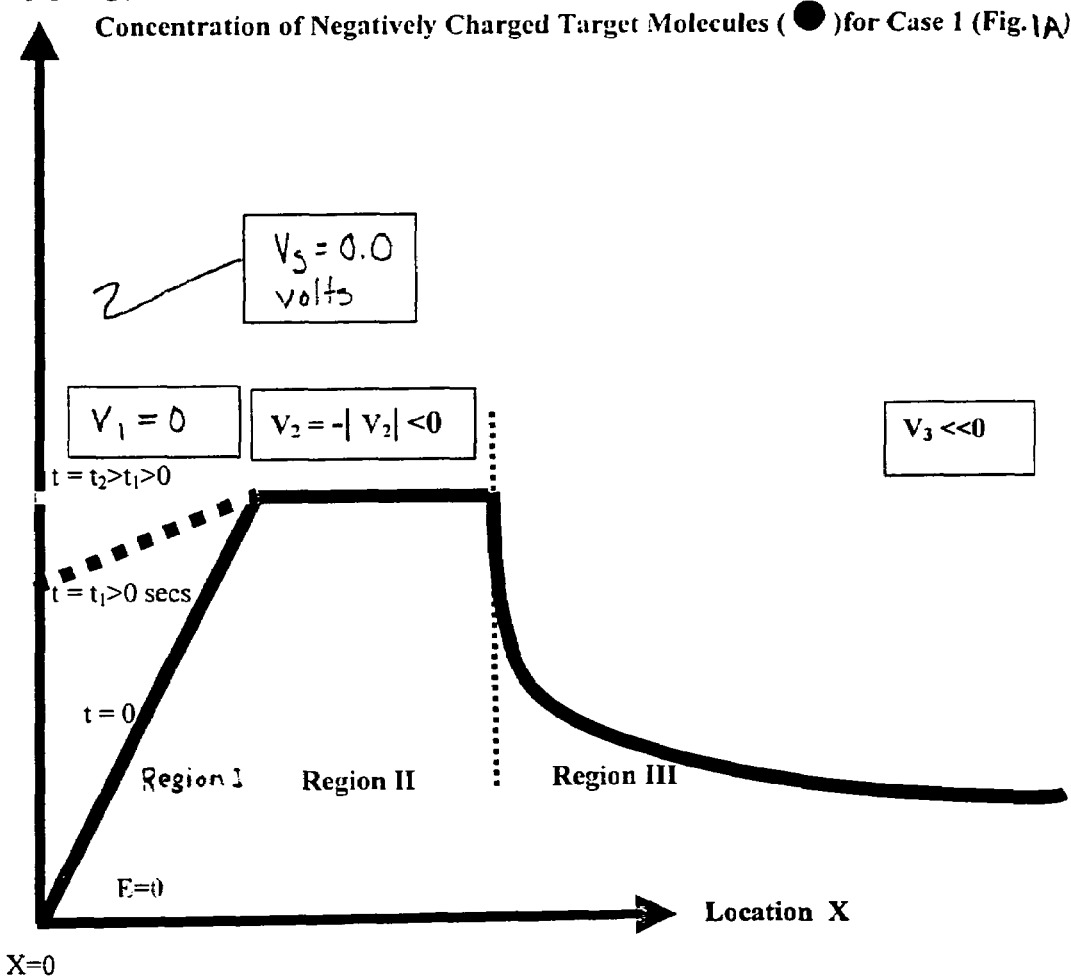
FIG. 2A shows transient features of the target biochemical concentration in Region I.
Figure 2B:
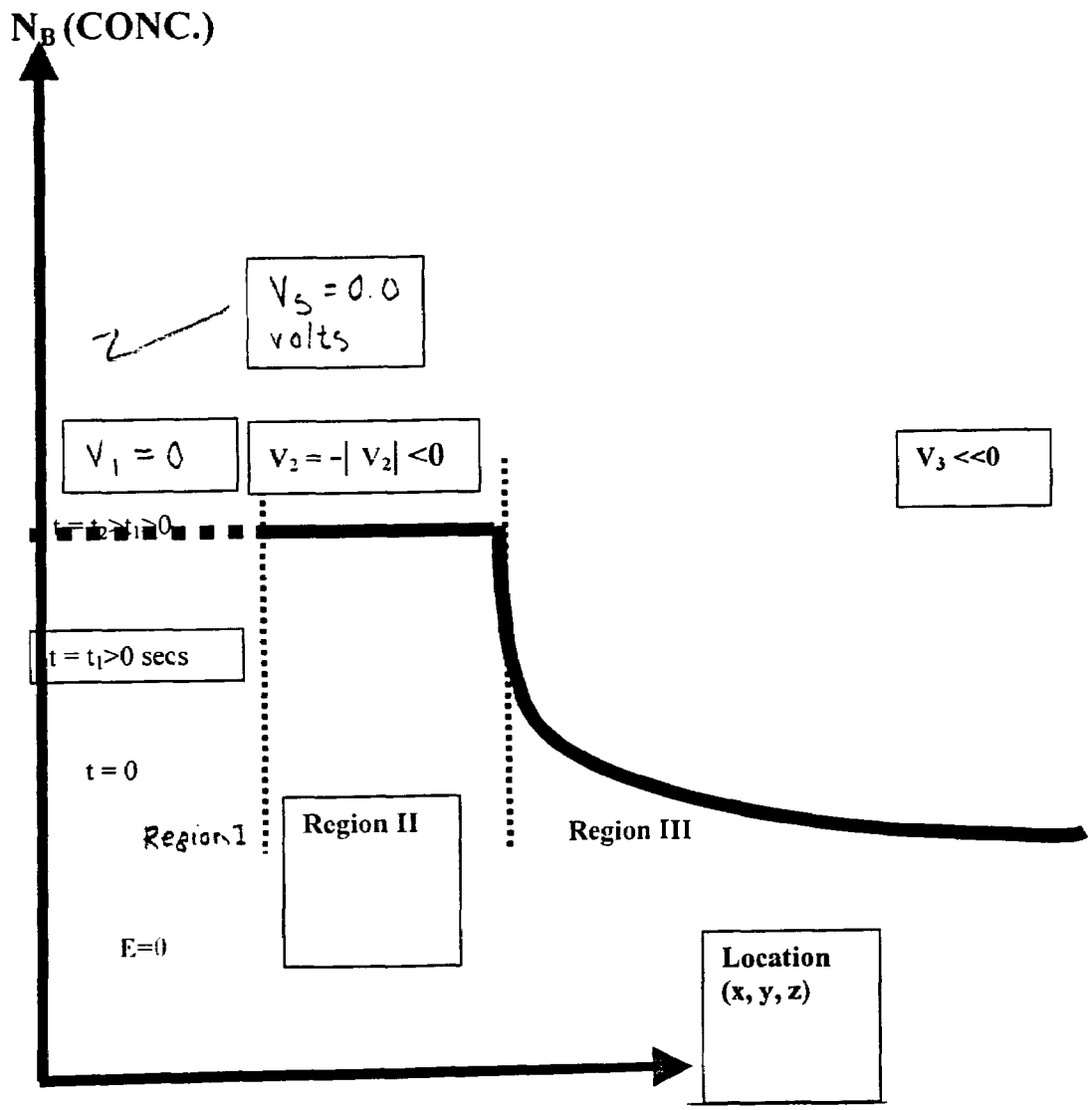
FIG. 2B shows steady state accumulated and Region I concentration increase of negatively charged target biomolecules after an appropriate time.

FIG. 2A schematically represents the concentration of charged chemicals in Region I as time progresses. The concentration reaches a high concentration value in Region I and is sustained in Region I with electric field E. The value of the concentration depends on the density of molecules available in Region II and the strengths of the various electric fields. FIG. 2B shows the steady state concentration of charged molecules in the various regions after steady state is achieved. The detailed values of the concentrations are dependent upon the detailed values of the voltages, grid separation and electric field values in the various regions.

Figure 2C:
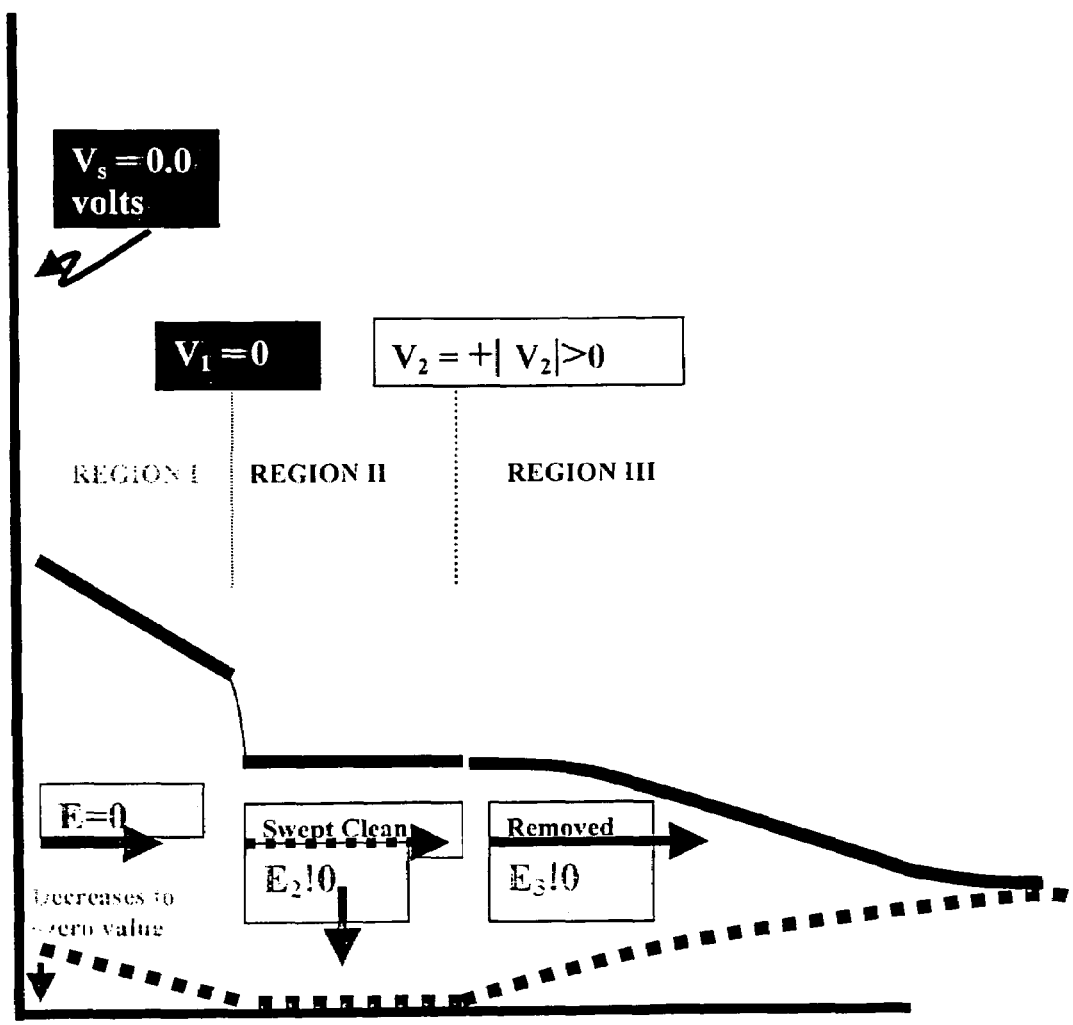
FIG. 2C shows concentration of negatively charged target molecules as a function of time t.
Figure 2E:
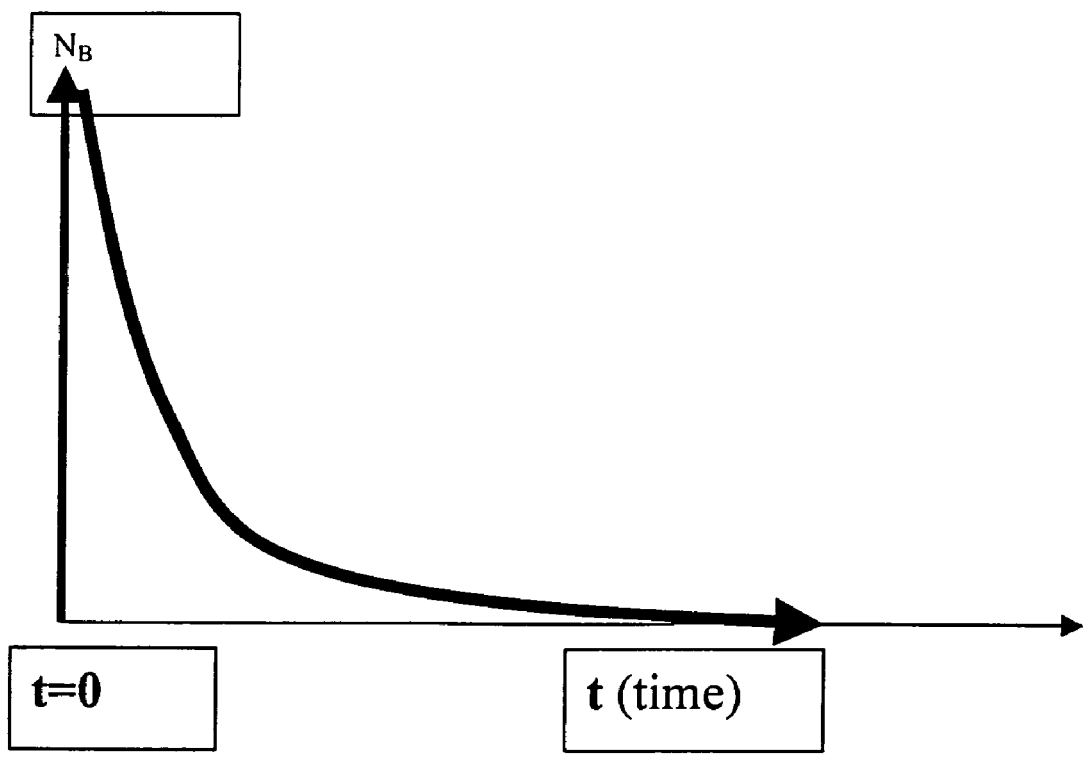
FIG. 2E shows concentration in Region I as a function of time t.

FIG. 2C shows the transient concentration (time dependent concentration) in the various regions when the electric field E polarity is chosen to remove charged molecules from Region II. The charged molecule concentration in Region II falls to zero rapidly. This sets a boundary condition of zero at the Region I-Region II interface. The target species in Region I then diffuse if there is no electric field in Region I, or drift if an electric field is applied in Region I between the sensor and grid 10. The concentration of target molecules in Region I thus falls to zero rapidly leaving Region I void of target molecules, as shown in FIG. 2D. As more target molecules dissociate from the sensor receptor binding, as shown in FIG. 1C, they too are removed rapidly from Region I. The time dependent dissociation of targets from receptors is measured, providing a convenient and rapid quantification of the dissociation dynamics and dissociation constant of the receptor-target pair. Both Regions I and II are void of target molecules in this example after a short time and thereafter, as shown in FIG. 2D.

FIG. 2E shows the measured concentration of bound chemical targets on the sensor as time proceeds and dissociation occurs. This curve provides the key dissociation constant and related information for the receptor-target pair.

FIG. 3 indicated the number of different proteins in the blood as a function of the plasma concentration of the protein. This curve indicates that there is a huge concentration of proteins active in the human body and that most of them are of very low concentration. Most plasma proteins, including potential diagnostic markers and drug targets, are present in the plasma in only tiny quantities.

The binding rate is measured with this system by rapidly increasing the concentration of the target molecules in the sensor vicinity and monitoring the sensor for the concentration of bound targets over time.

One application is to remove selective biochemicals from a pre-selected region. This is done to control the biochemical concentration in the pre-selected region.

In particular, by the removal of a particular target molecule, or the control of its concentration in a particular region, e.g., Region I of FIG. 1, the binding reactions of the molecule and its binding complement receptor concentration are controlled. The binding or the dissociation conditions for the pair are controlled.

One application is to use the system to measure and characterize the dissociation features of the molecular pair, or more than two biochemicals if appropriate. The binding rate is measured. The dissociation thermodynamics and dissociation constant are also measured and characterized. While this fundamental information is important scientifically, it also has significant specific applications. Medical diagnostics and drug discovery are two major applications. For example, it is known that the ratio of the concentrations of about four different proteins in blood plasma is a reliable indicator of the early stages of ovarian cancer, providing early enough diagnosis virtually ensures the patient is cured of the disease. Thus, the application of the invention to measurement of target concentrations is of importance and shows additional utility of the invention.

One application is for drug discovery in support of binding strength and concentration dissociation dynamics measurement. Other applications include selective management of charged biochemicals in a pre-selected biochemical sensing region.

Drug discovery depends on measurement of binding strength between the biochemical receptor and a drug candidate. Such a receptor may be a protein, RNA or DNA, or some other receptor such as a nerve synapse or opiate receptor in the brain for pain control. One method of determining the drug reactivity is to study the details of the dissociation dynamics.

Multiple studies may be performed simultaneously by using an array of "drug targets" and studying the binding features of the "candidate drug" with the drug targets. A Si biosensor currently under development is fully compatible with large arrays, integrated addressing circuitry on chip, electronic readout and automated testing, at low cost. The charge sensing device operation is described elsewhere. The present invention is not limited to any one type of sensor.

The invention lends itself well to studying the fundamental binding kinetics of biomolecules to specific binding chemicals. That fundamental information is of interest to the scientific community.

In FIG. 1A, a Region I concentrator 1 is an ion or species concentrator or de-concentrator. It concentrates biochemicals into Region I, thereby raising the biochemical target species to affect binding to pre-selected complementary receptors that are complementary chemicals that bind specifically to the target molecules. The system operates by attracting a high concentration of target ions to the interface 16 of Regions I and II, where a grid 20 is located and to which a voltage $V_1$ has been applied. Negative ions 2 drift to Region I $0>V_1>V_2=-|V_2|$. Grid 20 attracts negative ions through Region II and from grid 30. Ions diffuse or drift through Region I from grid 20 to the immediate vicinity of the sensor 10 where they bind if the target(s) are specific to the receptors 4 that have been placed on the sensor 10.

The end product in this mode of operation is an increased concentration of the target biochemical species in Region I, i.e. in the immediate vicinity of sensor 10. The system may also be used as a de-concentrator as represented on the following figures. Negative or positive ions 2 may be used; a negative ion is shown by way of example. Voltage polarities are selected as appropriate for the type of ion. ● indicates negatively charged biochemical or other negative ions. E is an electric field.

FIG. 1B shows a Region I biochemical removal device 41. Here, the same basic system if used as illustrated in FIG. 1B. Negative ions 2 diffuse ($E_I=0$) or drift ($E_I \neq 0$ and negative) out of Region I and into Region II. Here $0<V_1<V_2=+|V_2|$ if only diffusion is desired. By making the distance between grid 20 (interface of Regions I and II) small, diffusive transport is fast. Grid 20 repels, grid 30 at interface 18 between Regions II and III attracts negative ions through Region II to Region III. The above assume negatively charged ions. If ions are positively charged, then the voltage polarities are reversed for removal of biochemicals from Region I. For diffusion, both the sensor and grid 20 are at the same potential, e.g. grounded. For drift through Region I, the voltage on grid 20 is applied appropriate for drift removal of the ions from Region I. Only the diffusion condition for Region I is illustrated. ○ indicates negative ions.

FIG. 1C shows Region I ion removal as target biochemicals dissociate from the sensor surface. Negative ions diffuse if E=0 or drift if $E_I \neq 0$, and have correct polarity, out of Region I to grid 20 located at the interfaces between Regions I and II. Ions arriving at the grid 20 between Regions I and II are swept out of Region II by an electric field 6, and into Region III where they may be further removed. In this manner, Region I is kept devoid of target molecules as they dissociate from the sensor surface. ● represents negatively charged biochemical or other negative ions. E is an electric field.

FIG. 1D shows a two grid spherical biochemical removing device. The device operates the same as the rectangular grid structures of FIGS. 1A, 1B and 1C for either biochemical accumulation or biochemical removal. The difference here is a spherical geometry. Other geometries may be used as well. A small dotted arrow represents force 42 on negatively charged biochemicals. A medium dotted arrow represents applied electric field 6. A solid arrow represents flux 44 of biochemicals.

FIG. 2A shows transient features of the target biochemical concentration in Region I. Here there is no electric field in Region I, and diffusion transports the biochemicals to the location X=0 (origin) where the biochemical reacts with a specific receptors, other chemical which binds selectively to the target biochemical, e.g. as found on the surface of a biosensor. As the receptors begin to bind the target molecules, the concentration distribution in Region I, straight line, begins to rise eventually coming to the same concentration as in Region II. This concentration profile corresponds to the situation schematically illustrated in the concentrator FIG. 1A.

FIG. 2B shows steady state accumulated and Region I concentration increase of negatively charged target biomolecules after an appropriate time. This concentration profile corresponds to the steady state concentration which is found after some appropriate time has passed, a time adequate for the processes in FIG. 2A to have completed. The voltage polarities and arrangement are as described in FIG. 1A. Here the concentration of target ions in Region I is significantly increased due to the processes of drift and/or diffusion, as explained above and illustrated in FIG. 2A.

FIG. 2C shows concentration of negatively charged target molecules as a function of time t. Here the polarities are as indicated in FIG. 1C. And, either drift or diffusion removes the target ions from Region I. The removal over time is indicated.

At time t=0 seconds, an electric field $E_{II}$ ($\neq 0$) is applied to sweep away the charged biochemicals (target biomolecules) from Region II to Region III, thereby dropping the biochemical concentration $N_B$ in Region II as time increases. The result is that that the target biochemical species concentration in Region I diffuses out to the electrode grid 20 between Regions I and II and from there is swept across Region II to Region III. In a short time, determined by dimensional features and voltages applied, Region II becomes essentially devoid of target molecules. This sets up a boundary condition at the I-II interface of $N_B=0$ causing the concentration of biochemicals in Region I to diffuse to Region II (and be swept away) as indicated in FIG. 1B. Rapidly, the free biochemicals in Region I diffuse to Region II, and the free biochemical concentration in Region I drops to zero leaving only those target biochemicals remaining bound to the receptors on the sensor surface. As time proceeds, bound target molecules dissociate from the sensor surface at a rate determined by the dissociation constant for the target species and its surface binding partner. Thus, as shown in FIG. 1C, Region I remains essentially empty of the target species with only dissociation occurring (without re-association because of the free biochemical removal). If an electric field is applied in Region I, the removal of target molecules from Region I is assisted (adds to the diffusion removal). Using either electric field drift, or diffusion, or both transport means causes the removal of dissociating biochemical target species from the sensor surface. Thus, Region I remains essentially free of dissociated (free) target molecules at all times, and rebinding of the dissociated molecules is prevented.

Since the sensor measures the bound target molecules quantitatively, the rate of sensor output parameter change directly provides the dissociating rate of the target biochemical species including the dissociation constant and thermodynamic dissociation details.

The target biochemical free concentration continues to remain zero in Regions I and II until all bound target molecules have dissociated and been removed. Region III has a concentration dependent upon the competitive features of drift due to electric field and diffusion due to concentration gradient features.

FIG. 2D shows target molecules free carrier concentration steady state for conditions shown in FIG. 1C. Concentration of negatively charged free target molecules correspond to the conditions represented in FIG. 1C. Dissociating molecules are immediately removed form Region I, delivered to Region II to be swept away to Region III.

FIG. 2E shows concentration in Region I as a function of time t. The removal of the biochemical concentration $N_B$ over time depends on the electric field value in Region I or on the diffusion rate of biochemicals out of Region I, as shown in FIG. 1B, to Region II where they are swept away by an electric field. The distance between the sensor S and the grid at the Region I-II interface is kept very short to ensure diffusion if diffusion removal is used. The removal time is chosen to be short compared to the dissociation decay time.

FIG. 3 shows protein concentration, in molar concentration, in blood plasma versus the number of proteins. FIG. 3, taken from Science magazine, indicates that there are huge numbers of proteins of very low concentration in blood plasma. The implication is that these proteins are important to body function, immune system behavior, physiological function and human health. These low concentration proteins cause a major problem in detection for human health and disease diagnostics.

A group of invention embodiments is shown in FIG. 4A-8B. This group is not all-inclusive and other derivative inventions may be created using the information provided in this document.

Figure 4A:
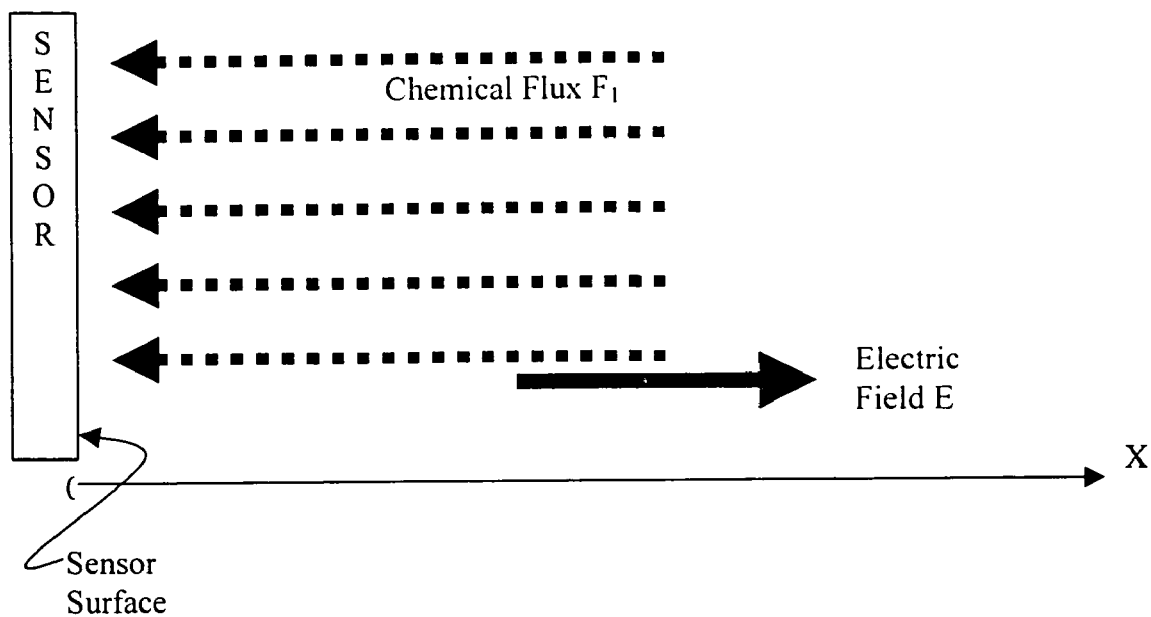
FIGS. 4A and 4B show a first biochemical concentrator embodiment.
Figure 4B:
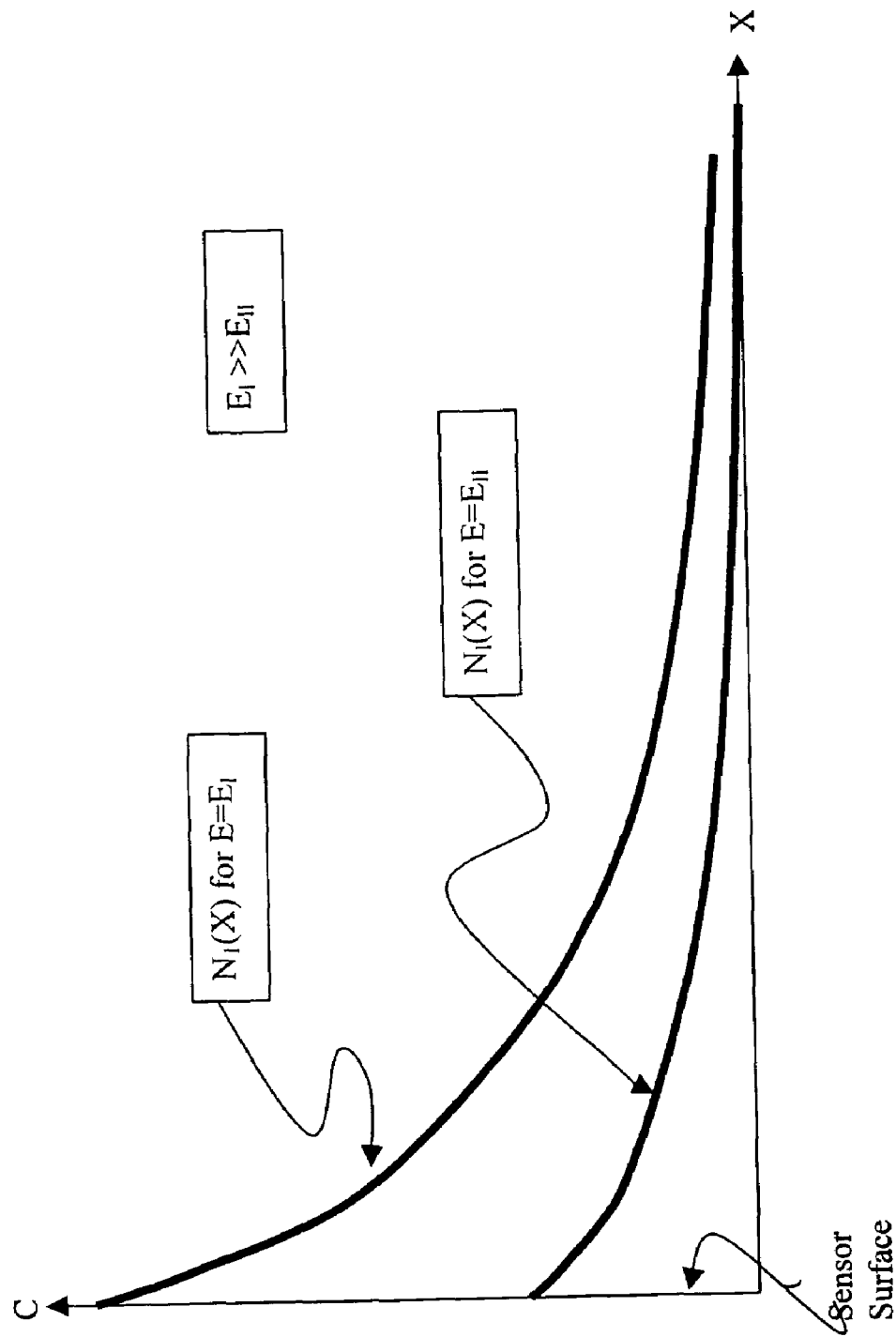

FIGS. 4A and 4B show a first biochemical concentrator embodiment. The sensor with a bias voltage applied and resultant electric field in the analyte region is schematically represented. FIG. 4A represents an electric field (E) configuration as a function of location X. FIG. 4B schematically represents the concentration profile $N_1(X)$ for two electric field values ($E_I \gg E_{II}$). The different surface concentrations $C1_I$ and $C1_{II}$ resulting from the two different electric field strengths are represented. FIG. 4B shows target concentration versus X for two different values of electric field $E_I$ and $E_{II}$, where $E_I \gg E_{II}$ for the embodiment schematically represented in FIG. 4A.

Figure 5A:
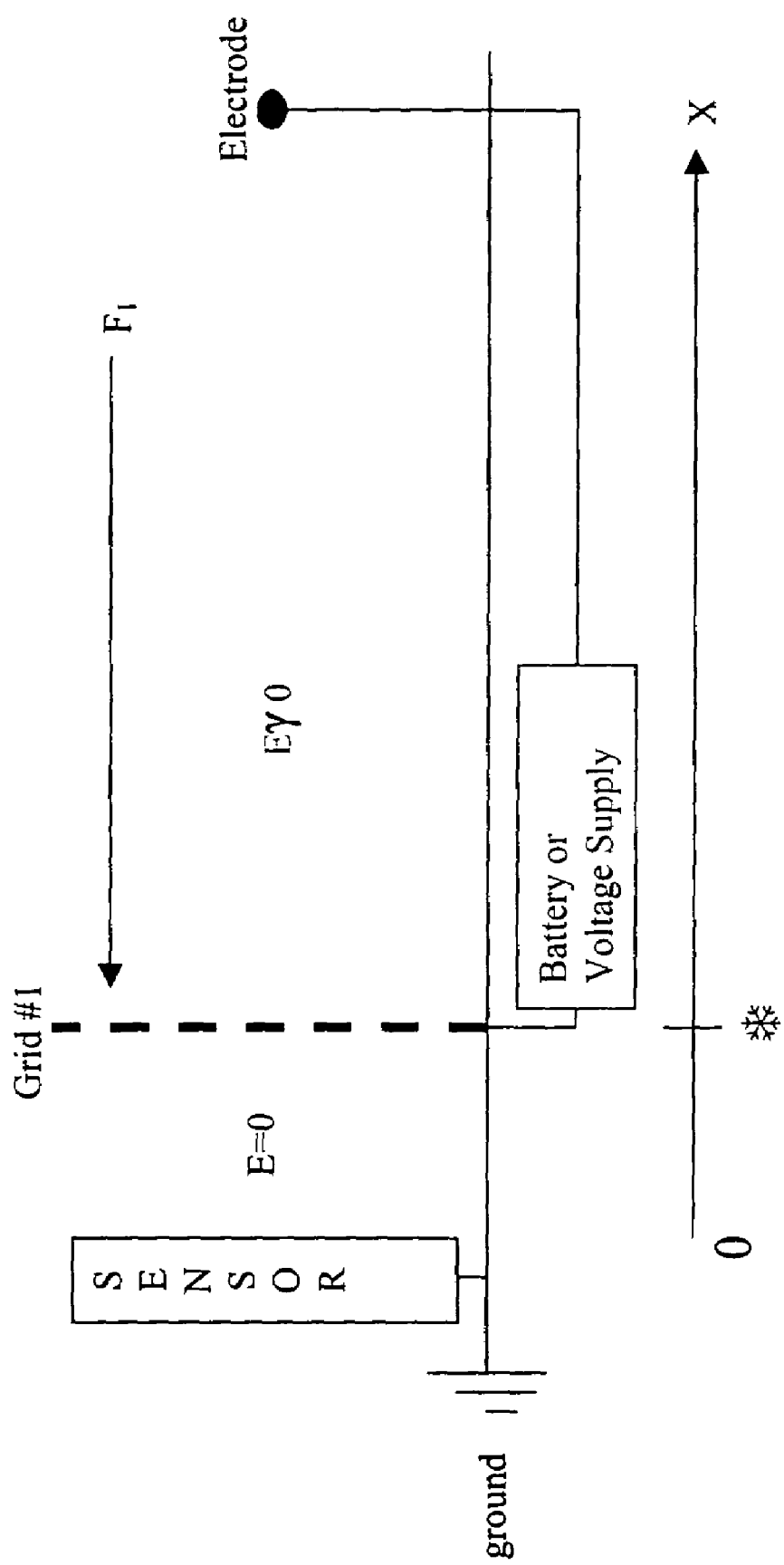
FIGS. 5A and 5B show a second biochemical concentrator embodiment.
Figure 5B:
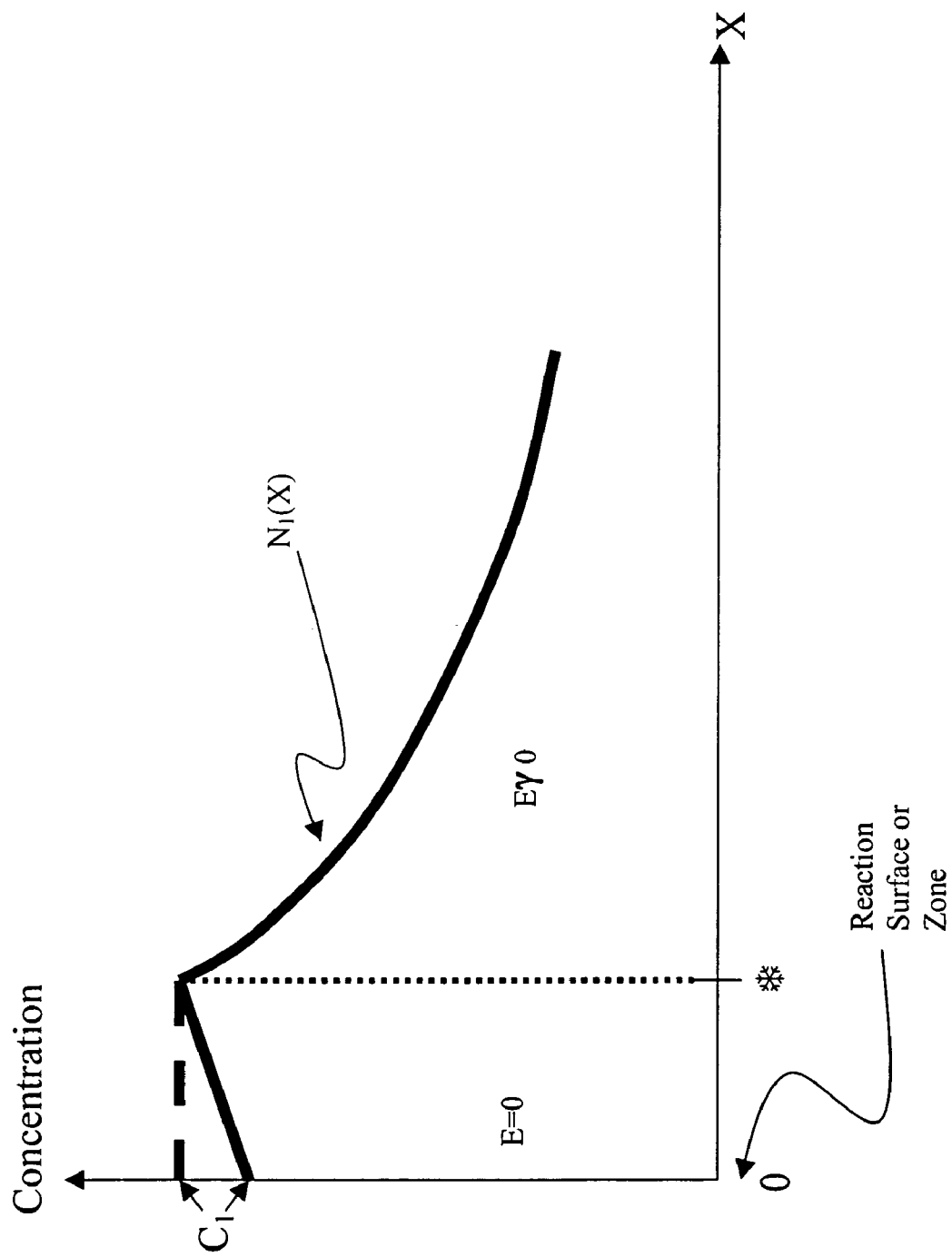

FIGS. 5A and 5B show a second biochemical concentrator embodiment. FIG. 5A schematically shows a sensor and electrical grid placed in a biochemical sampling and testing region, shown biased with a battery. The sensor is connected to the grid G1 and both are grounded to one side of a battery. The other electrode (not shown) drops the battery voltage from that electrode to the grid G1. FIG. 5B shows the concentration $N_1(X)$ at the sensor surface, in the region between the grid and the sensor and between the grid and an electrode placed in the target environment. The region to the left of ✱ is free of applied electric field.

Figure 6A:
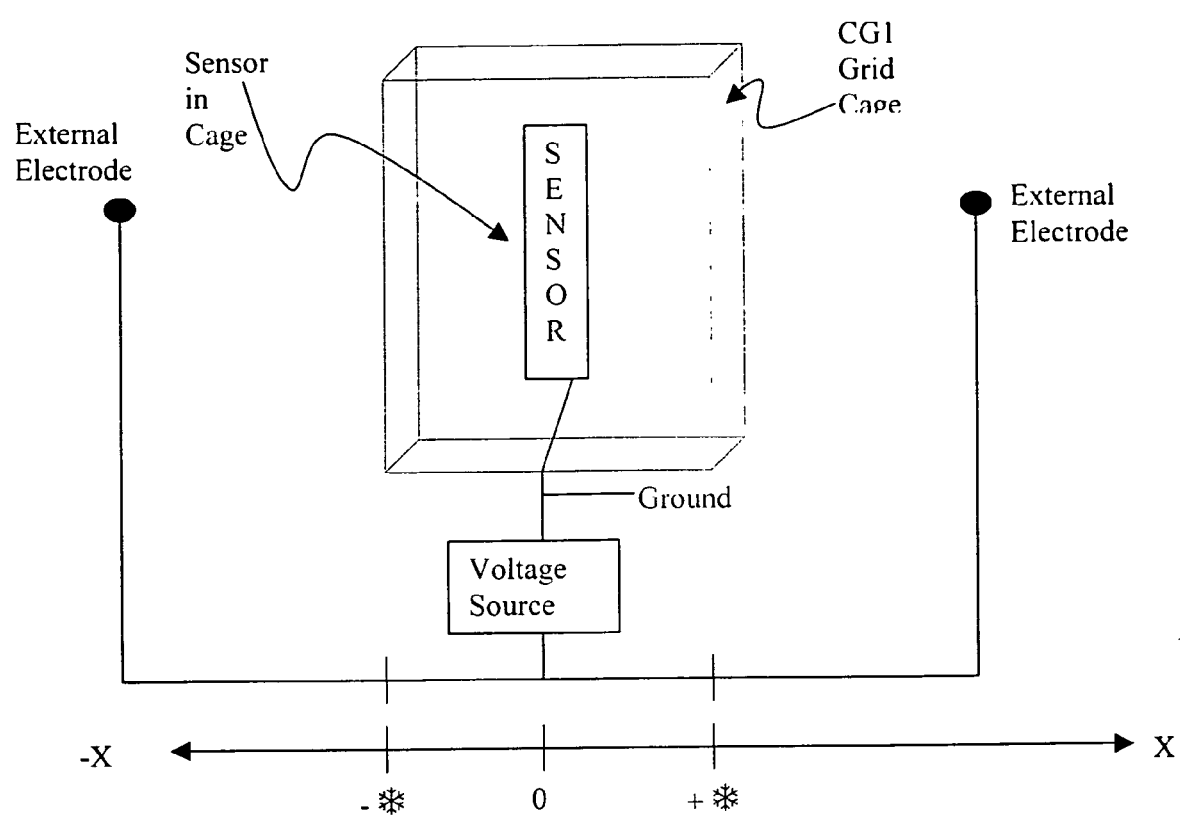
FIGS. 6A and 6B show a third biochemical concentrator embodiment.
Figure 6B:
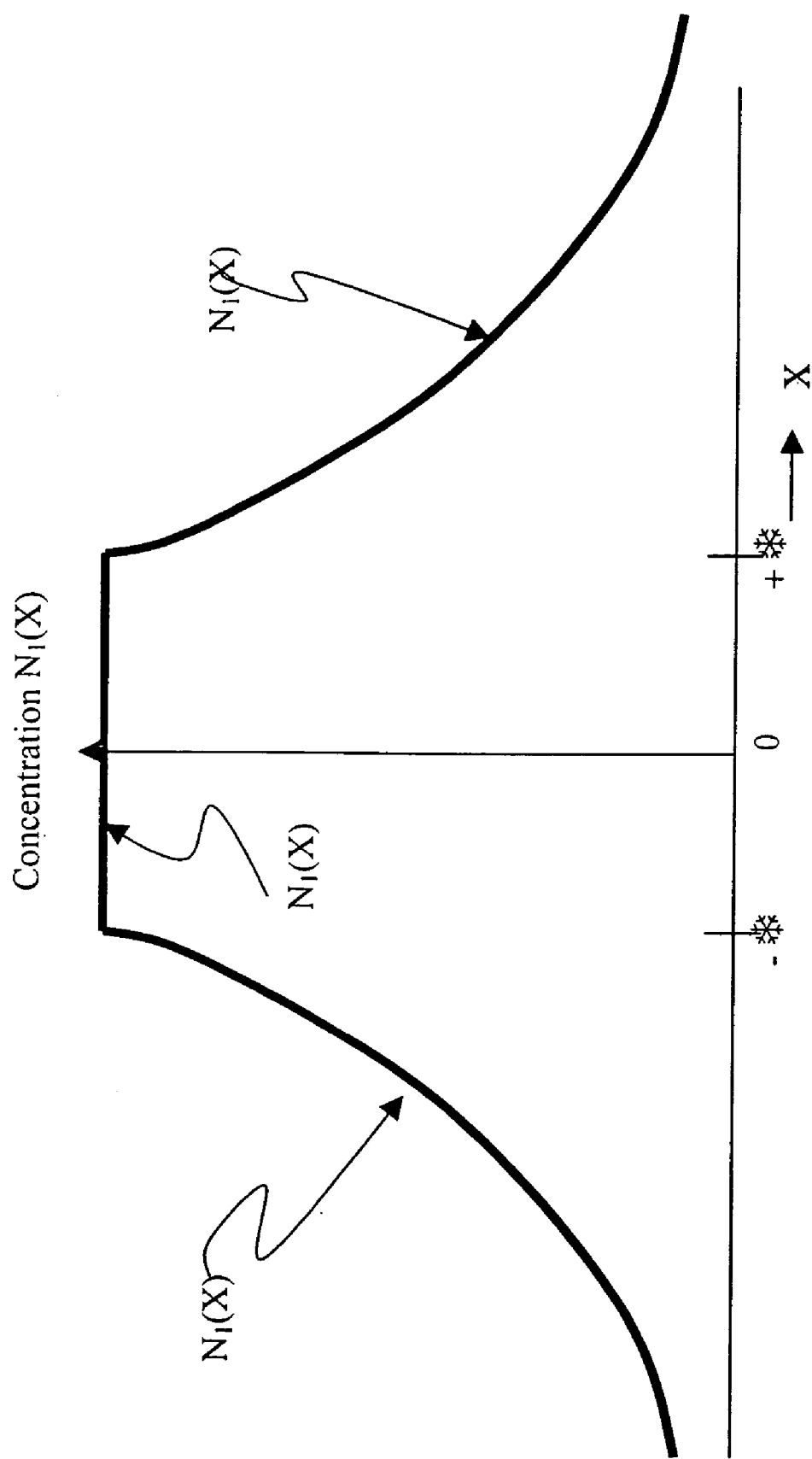

FIGS. 6A and 6B show a third biochemical concentrator embodiment. FIG. 6A shows sensor for detecting a target species S1 is placed in a three-dimensional electrode cage. Both electrode cage and sensor are grounded. A battery biases an electrode in the collection region. FIG. 6A is a schematic representation of the sensor in a cage with both cage and sensor at ground or common potential voltage. A voltage is applied outside the grid cage and a voltage drop between this outside region and the cage is applied with attendant electric field E. FIG. 6B shows the resulting a concentration profile $N_1(X)$ of the target species S1 both inside and outside of the cage. The example shown is for a situation where the sensor receptors are already saturated to the maximum value permitted by the mass action law. FIG. 6B is a schematic representation of the target concentration inside and outside the grid cage GC1.

Figure 7A:
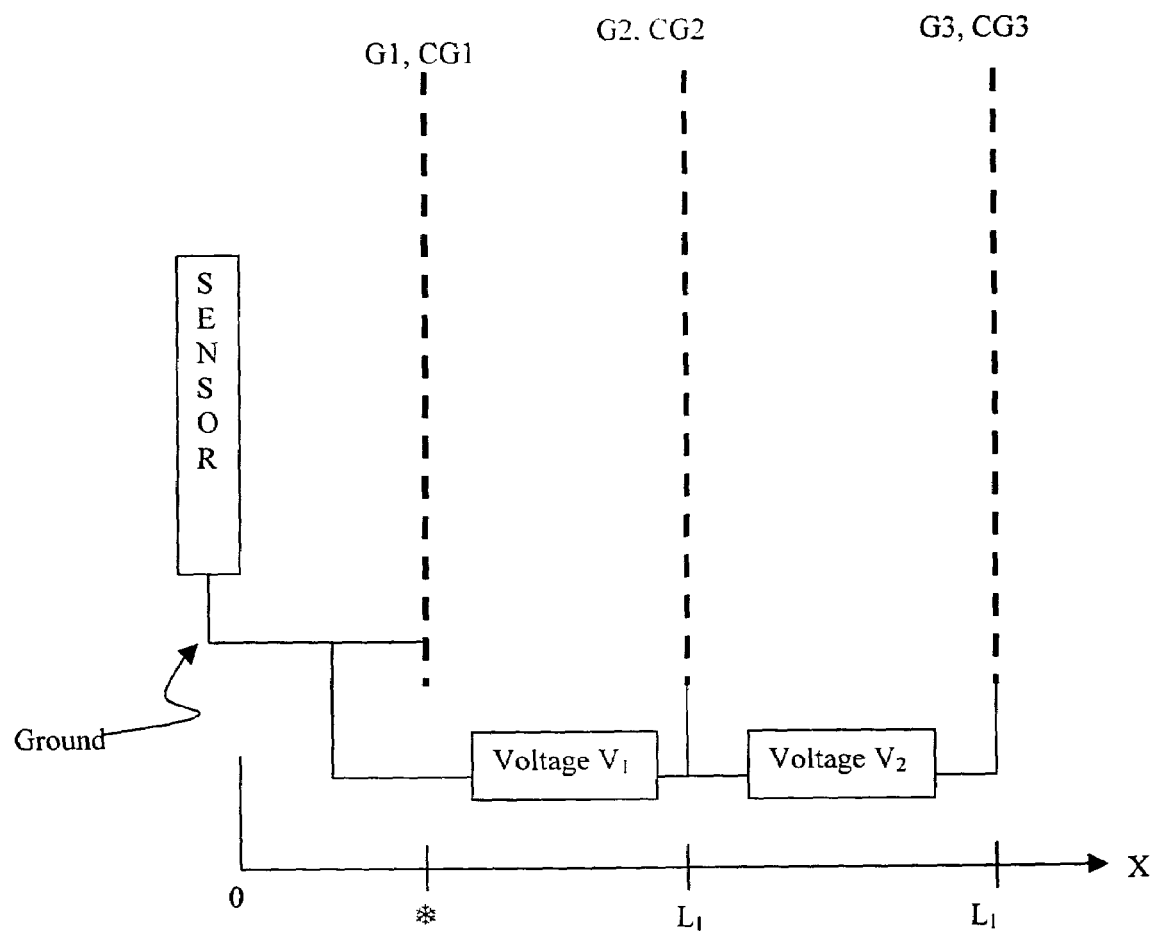
FIGS. 7A and 7B show a fourth biochemical concentrator embodiment.
Figure 7B:
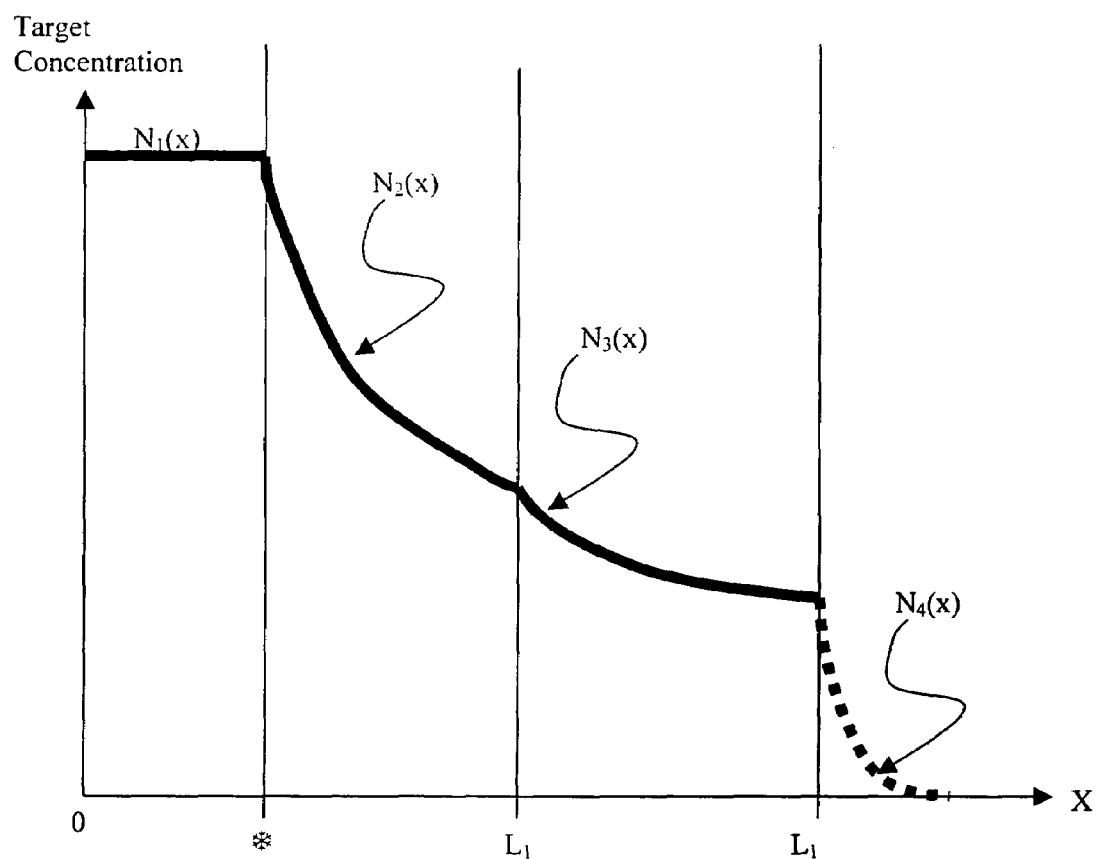

FIGS. 7A and 7B show a fourth biochemical concentrator embodiment. FIG. 7A schematically represents a biochemical collection systems comprising a sensor, and three external electrodes, the first of which is located a distance 6 from the sensor and, with the sensor, grounded. The electrodes may be grids (G1, G2, G3), wires or cages (CG1, CG2, CG3). Electrode 2 (C2/CG2) is biased at a first voltage with respect to the first electrode (C1, CG1). Electrode 3 (C3, CG3) is biased at a second voltage with respect to electrode 2 (C2, CG2). Multiple collection zones are supported. A three cage grid system is represented in a cross sectional view with power supply connections. An example of target S1 concentration profiles $N_1(X)$ are represented in FIG. 7B for the different collection regions.

Figure 8A:
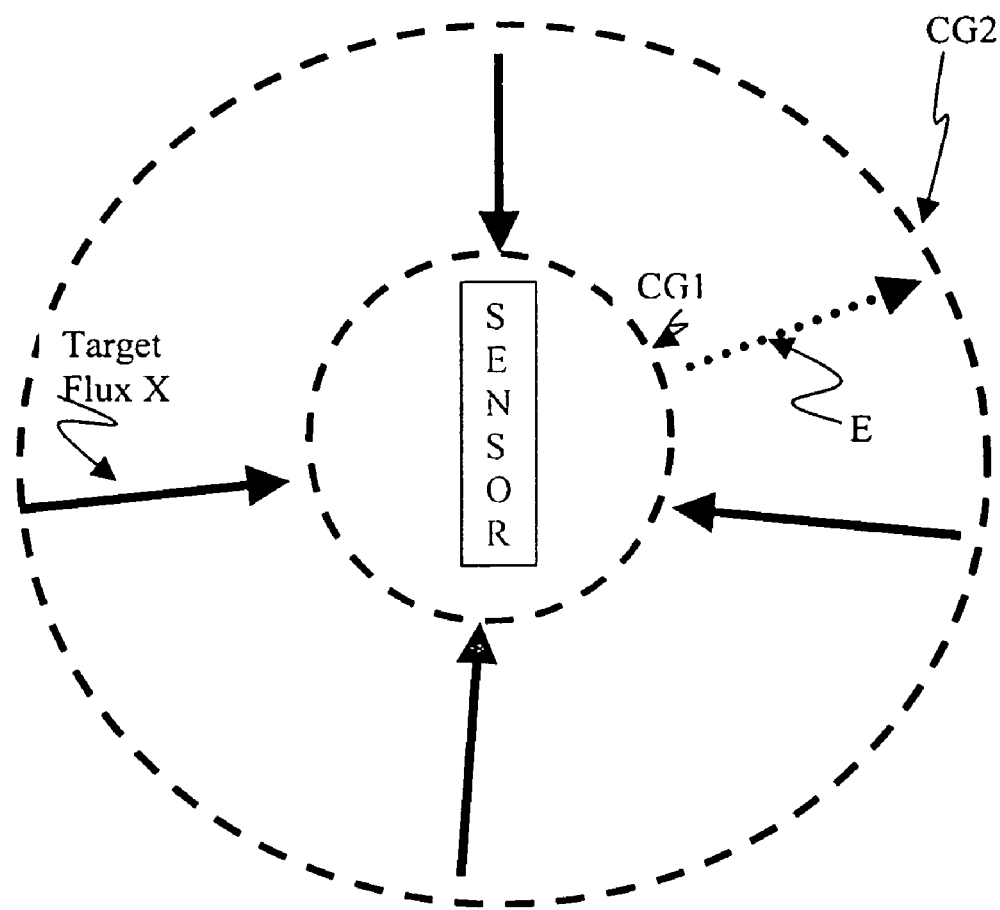
FIGS. 8A and 8B show a fifth biochemical collection embodiment.
Figure 8B:
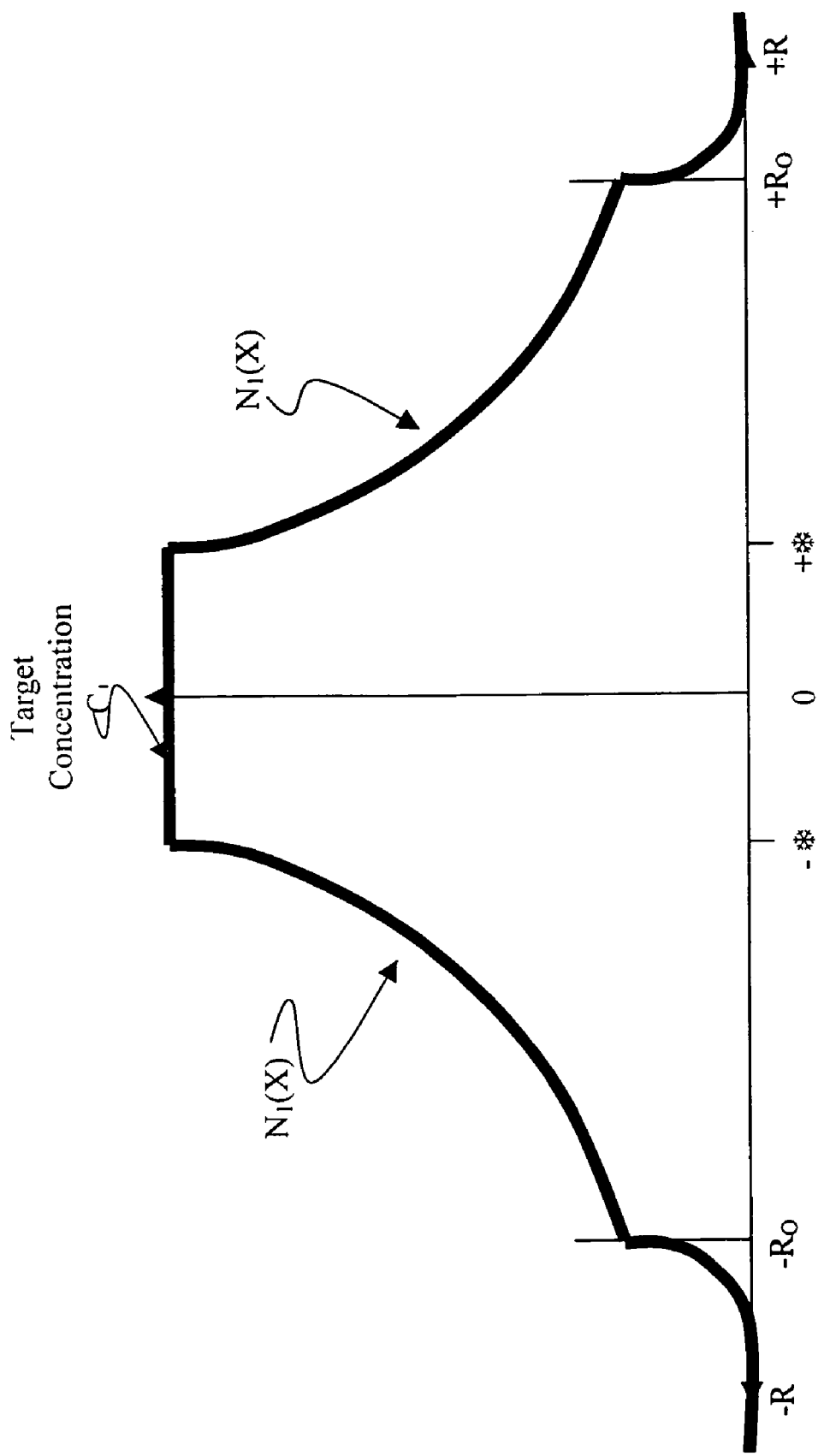

FIGS. 8A and 8B show a fifth biochemical collection embodiment. FIG. 8A schematically represents a multiple electrode systems similar to that schematically represented in FIGS. 7A and 7B except that the cages CG1 and CG2 are of dimensions and location such that the electric field arising from the voltage applied between these two electrodes is non-homogeneous, and, in this example, much higher in the vicinity of the first electrode cage CG1. FIG. 8A shows a spherical cage embodiment example. The power supplies are not shown. The sensor is grounded to CG1 and a voltage drop applied between CG1 and CG2. FIG. 8B shows a target concentration profile representation for spherical cage configuration. A high target concentration is maintained in the immediate region of the sensor.

Figure 9:
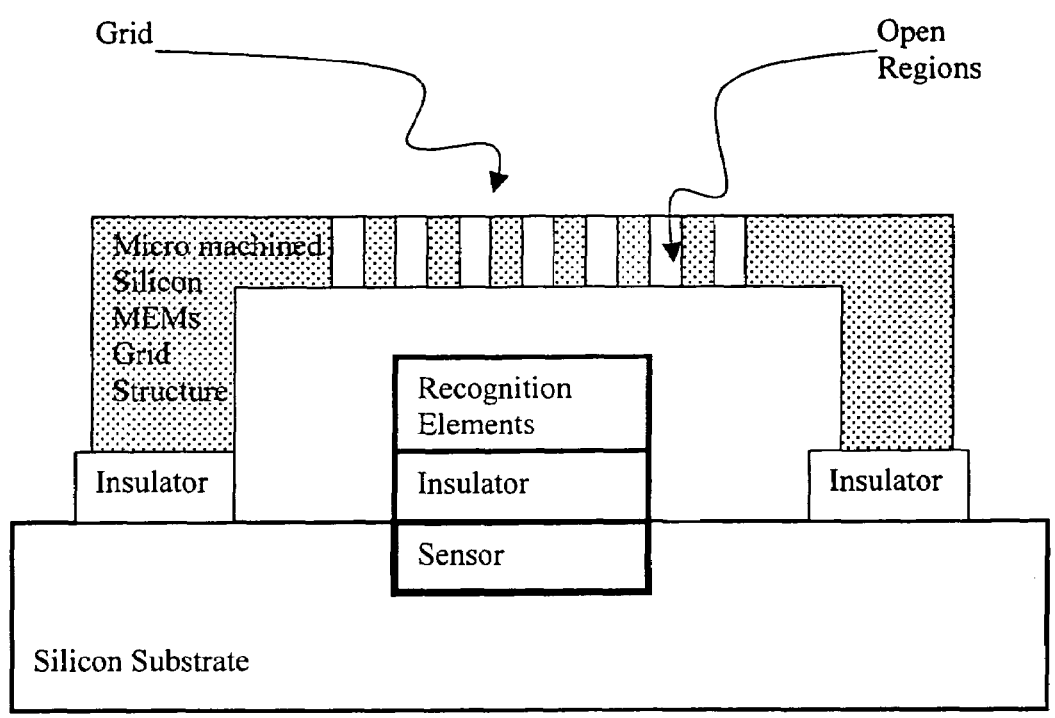
FIG. 9 is a schematic representation of a micro machined Si grid structure married to a sensor chip.

FIG. 9 is a schematic representation of a micro machined Si grid structure married to a sensor chip. FIG. 9 is a cross section of MEMs fabricated grid structure. No biases are shown. A grid chip is bonded to another sensor Si chip in a manner known to one of ordinary skill in the art.

FIG. 4A schematically represents the movement of a target species $N_1$ towards an electrode, labeled sensor, due to charge species "drift" arising from an applied electric field E. The flux of target molecules (S1) $F_1$ is dependent upon the strength of the electric field E. FIG. 4B represents the species S1 concentration as a function of location X measured from X=0. X=0 is at the sensor face. The concentration $C_1$ of species S1 at the sensor surface (X=0) is directly related to and dependent upon the strength of the electric field. The concentration fall off profile is determined by the strength of the applied electric field (and its distribution if the electric field is not constant) and the diffusion coefficient of the target species in the test environment, which is generally a solution. It should be noted that there may be many biochemical species present and that each will have its own concentration profile and concentration at X=0.

For different electric field strengths, the concentration C1 (value of $N_1$ at X=0) for species S1 will be affected by the strength of the applied electric field, as will the rate of delivery of species S1 to X=0. FIG. 4B shows schematically two examples of species 1 concentration profiles resulting from two different applied electric fields $E_I$ and $E_{II}$. The resulting species 1 profiles are different and, most importantly, the concentration of species 1 at X=0, $C_{1A}$ and $C_{1B}$ are such that $$C_{1A} \gg C_{1B}$$

When $$E_I \gg E_{II}$$

That is, the strength of the electric field directly affects the target species concentration $C_1$ at the sensor receptor interface. Thus, in this embodiment one would like a high electric field in the immediate vicinity of the receptor species and target species, i.e. at the sensor reaction region, where concentration of the target species is an issue as it is for toxins such as botulinum toxin. However, there may be strong motivation for eliminating or reducing the electric field strength in the immediate vicinity of the chemical reaction (binding) region.

The electric field may be eliminated from the immediate vicinity of sensor. Since many receptor molecules have geometrical features that influence their binding, and the net charges are distributed at different locations on the molecule, a high electric field may cause distortion of the receptor molecule. For example, a large folded antibody which has geometrical features affecting its binding to a target molecule, may be distorted by the electric field. Examples include, but are not limited to antibodies, proteins, DNA fragments, RNA fragments and oligos. Such distortion of either the target molecule or the receptor molecule is undesirable since such may in turn affect specificity of reaction and the reaction rates. Non-specific reactions create false positive signals from the sensor and are to be avoided or minimized.

While it may be desirable to eliminate or minimize the electric field in the immediate vicinity of the receptor and target binding region, the inventions described herein, and their usefulness, are not limited to regions where the electric field is zero. Where one may for some reason wish to have some electric field present in the vicinity of the target/receptor reaction, the basic inventions described herein remain useful.

Where elimination or reduction of the influence of an electric field on chemical species in the immediate vicinity of the receptor target reactions is desired, another sensor embodiment is employed. A specialized structure is constructed to keep the sensor region at a constant voltage without the applied electric field terminating on the sensor surface. FIG. 5A schematically represents such a sensor configuration.

An attractive voltage biasing arrangement is showing in FIG. 5A where the sensor and grid G1 are at ground and the solution is biased at a net applied voltage V. Here a grid structure G1 acts as a voltage terminal and is connected to the sensor to provide a zero electric field between the sensor active region and the grid structure G1. Here the target species concentration builds up at the grid electrode G1 as in FIG. 5B. Actual delivery of the target species S1 to the receptors occurs, however, by diffusion. Since the target species concentration at the grid G1 can be made very high using the electric field concentrations method, and the grid G1 can be placed in very close proximity to the sensor receptor region, a high concentration and a high concentration gradient of the target species between the grid G1 and the sensor can be achieved. This results in a high diffusion rate of the target species S1 to the sensor surface and a high concentration of the target species S1 at the sensor surface (X=0), as shown in FIG. 5B. A high target concentration at the receptor site causes an increased binding rate and results in a higher equilibrium [S1S2] concentration or product [P]. Further, the sensor achieves a pre-selected sensitivity threshold in a shorter time than if the target species is not concentrated.

By using the invention in the second embodiment, the concentration of target species S1 is high and ensures a high bound species/receptor concentration P at the sensor surface, a related strong sensor output signal, and a fast sensor signal response to the presence of the target molecule in the environment being sampled.

Design features include magnitude of the applied voltage, time dependence of the applied voltage, container configuration, and importantly, the value of $\delta$. The dimension $\delta$ should be conveniently small or short to insure rapid diffusion form the grid cage CG1 to the sensor surface at X=0.

The third embodiment is similar to the second embodiment, except that the grid G1 is replaced by a cage CG1 as schematically represented in FIG. 6A. The concentration details mechanisms details are similar to those described in FIG. 5B, except that the cage configuration, under equilibrium, would result in a concentration configuration $N_1(X)$ as shown in FIG. 6B. That is, the concentration of the target species S1 is increased dramatically in the vicinity of the sensor and species S1 is in effect trapped (concentrated) within the cage and does not leave the cage. Reactions at the surface of the sensor with the specific receptor to form the bound pair drop the concentration $N_1$ of the target species S1 at the sensor surface until the receptors reach an equilibrium binding concentration as indicated by the appropriate mass action law and binding constant. Again, a small $\delta$ value provides faster concentration to a high value and also increases the diffusion delivery to all regions of the cage CG1, reaching a high concentration of the target species S1 rapidly. These two aspects of the third embodiment translate to high binding concentrations of the target S1 and strong signals at the fastest rates (detection sensitivity and speed of sensor response to threshold signal levels).

The fourth embodiment is represented schematically in FIG. 7A and extends and improves on the concepts represented in the first three embodiments by placing another electrode at a pre-selected location L in the sensor environment. The second electrode in FIG. 7A is either a grid FIG. 7A or another cage FIG. 7B. Here a first voltage is applied between the first and second grids at X=$\delta$ and L respectively, to drift the charged biochemicals to the $\delta$ location. If a second cage CG2 in FIG. 7B is used, the transport occurs in three dimensions. The location of the second grid region L and applied voltage between the grids G1 and G2 determines the electric field between the two grids and thus the rate of drift of species S1 to the sensor region, and the concentration of species S1 at the $\delta$ and within the cage and at location G1. A second voltage is applied between the sensor and said first grid at X=$\delta$ if desired.

FIGS. 8A and 8B schematically represents another invention embodiment. Here a non-homogeneous electric field allows for large special accumulation of the target molecules at relatively low voltages while ensuring a very high concentration of the target species S1 at the first cage CG1 location $\delta$. It is well known that placing a voltage between a point and a second electrode, such as a grid or a plate, concentrates a high electric field at the point with the electric field value falling off rapidly and significantly as one moves away from the point toward the plate/grid. While a "pointed" electrode provides good field concentration, other geometries can employ the same basic principle of electric field concentration.

FIG. 8A shows a configuration where the sensor and first cage CG1 are close together (small $\delta$) and a second cage CG2 at a distance and of radius L (CG2 is spherical in this example). FIG. 8B shows the electric field E profile versus radius R. Here a very large volume of the environment is sampled and target molecules are collected at a modest applied voltage value, while ensuring a high electric field required for high target chemical S1 concentrations is found at the first cage location ($\delta$) and in the sensor region. Thus, a very high concentration of target molecules is placed in the immediate environment of the sensors active surface (receptor locations) and these targets are collected from a three dimensional volume. The collection volume is selected with the details of the critical target molecule S1; a large sampling volume is desirable. Target accumulation speed is again influenced by the applied voltage values.

Another embodiment adds a third grid G3 or cage CG3. Here the voltage applied between the first grid G1 and second grid G2 is $V_1$. A second voltage source is applied between the second grid (or cage) G2/CG2 and the third grid G3/CG3. Using this configuration a very large volume can be sampled (the G1-G2 region) and the more rapid concentration (typically) in the volume between G2/CG2 and G1/CG1. Again, point concentration and other features described for various embodiments herein may be incorporated.

The different apparatus of the present invention are easily constructed. Grids can be made of any material that may be biased. For example, G1 can be a MEMs grid fabricated in very close proximity to the sensor surface. Alternatively a wire grid can be used. It is typically of a non-corroding material. Grids may be constructed of, for example, stainless steel meshes, or plated polymer meshes.

The invention may be integrated with other concentration methods and other applications. The simplicity of the inventions lends itself to easy integration with other useful devices and compatibility with different types of sensors. For example, one can add mechanical mixing. Various types of sensors can be placed at the target reaction location.

Numerous applications of the invention exist for application regimes. While the examples given herein often address biochemical concentrations needs, the invention applies to situations where one wishes to concentrate particle or chemical species. Examples include, but are not limited to: DNA fragments, RNA fragments, public health applications, medical applications, bioterrorism agent monitoring for defense, drug detection and discovery, chemical processing, and target molecule refining, among others.

The term receptor is a general term referring in this application to a generic lock and key pair component that provides a bonding feature (to a target) and a specificity features. Examples of receptors include, but are not limited to: antibodies, oligos and DNA and RNA components, nerve receptors, drug receptors, proteins, chemicals, heavy metals, explosive compound vapors, and drugs of all types. The term receptor as used herein thus is intended to represent a general recognition element. In this application, the terms receptor and recognition element are interchangeable.

Target molecules, by way of example, include, but are not limited to: disease causing agents such as viruses, fungi and bacteria epitopes, toxins, DNA, RNA, oligos and related compounds, proteins, antibodies, defensins, heavy metals and heavy metal compounds (Hg, Pb, and others), explosive compounds, he receptor list above, and many others.

The following is a symbol list and definitions as used herein:

S Biochemical or chemical species
C Concentration, normally at the sensor surface
X=0 Sensor surface location
X=δ First grid G1 location
$N_1$ Target species concentration (number/unit volume or molar concentration)
$N_2$ Concentration of receptor to target species (receptor to species)
P Concentration of bound receptor to target species (compound)
E Electric Field
$V_d$ drift velocity arising from an electric field E
$D_1$ Diffusion coefficient for species S1
● Mobility of a molecular species
G1 A grid
G2 A grid
G3 A grid
CG1 A cage grid
CG2 A cage grid
CG3 A cage grid
C Concentration of a species at a surface location (reaction region or surface of a sensor)

While the invention has been described with reference to specific embodiments, modifications and variations of the invention may be constructed without departing from the scope of the invention, which is defined in the following claims.

The invention claimed is:

1. A biochemical concentrator apparatus comprising:
a solution containing a target species,
one or more electric field generators for generating electric fields and for effecting movement of the target species within the solution and changing species flux within regions of the solution,
a sensor having receptors for the target species,
one or more voltage sources connected to the one or more electric field generators, and
further comprising a ground connected to the sensor and to the one or more sources,
wherein the one or more electric field generators can concentrate the target species in the region of the solution nearest the sensor and remove the target species from that region and from the vicinity of the one or more electric field generators, without necessarily applying an electric field in the area around the sensor during operation,
wherein the one or more electric field generators comprise one or more electrodes spaced from the sensor,
wherein the one or more electrodes comprise one or more grids surrounding the sensor and spaced between the sensor and each respective electrode's voltage source.

2. The apparatus of claim 1, further comprising multiple grids surrounding the sensor and multiple voltage sources connected between the grids.

3. The apparatus of claim 2, wherein the multiple grids are shaped for effecting concentrations of the species near the sensor.

4. The apparatus of claim 2, wherein the source provides pulsed, alternating, sinusoidal or other DC or AC power to the field generator.

* * * * *